United States Patent
Han et al.

(10) Patent No.: US 11,311,203 B2
(45) Date of Patent: *Apr. 26, 2022

(54) MICROCIRCULATION DETECTION SYSTEM

(71) Applicant: PixArt Imaging Inc., Hsin-Chu County (TW)

(72) Inventors: Wei-Ru Han, Hsin-Chu County (TW); Chih-Yuan Chuang, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 432 days.

This patent is subject to a terminal disclaimer.

(21) Appl. No.: 16/355,864

(22) Filed: Mar. 18, 2019

(65) Prior Publication Data

US 2019/0209026 A1    Jul. 11, 2019

Related U.S. Application Data

(63) Continuation-in-part of application No. 15/996,652, filed on Jun. 4, 2018, now Pat. No. 11,020,013, which
(Continued)

(30) Foreign Application Priority Data

Jan. 29, 2015 (TW) ................. 104103138
May 25, 2015 (TW) ................. 104116752

(51) Int. Cl.
*A61B 5/02* (2006.01)
*A61B 5/026* (2006.01)
(Continued)

(52) U.S. Cl.
CPC ............ *A61B 5/0261* (2013.01); *A61B 5/015* (2013.01); *A61B 5/0295* (2013.01);
(Continued)

(58) Field of Classification Search
CPC ... A61B 5/0261; A61B 5/4848; A61B 5/4884; A61B 5/0295; A61B 5/742; A61B 5/015;
(Continued)

(56) References Cited

U.S. PATENT DOCUMENTS

| | | | |
|---|---|---|---|
| 2003/0233048 A1 | 12/2003 | Silverman et al. | |
| 2009/0220189 A1* | 9/2009 | Kiesel ................. | G01J 3/02 385/12 |

(Continued)

FOREIGN PATENT DOCUMENTS

| | | | | |
|---|---|---|---|---|
| CN | 1387824 A | 1/2003 | | |
| WO | 2011/026986 A1 | 3/2011 | | |
| WO | WO-2011026986 A1 * | 3/2011 | ......... | A61B 5/02416 |

OTHER PUBLICATIONS

Widmer, R. Jay, et al. "The origin of the biphasic flow response to local heat in skin." Microcirculation 15.4 (2008): 349-357. (Year: 2008).*

*Primary Examiner* — Andrey Shostak
(74) *Attorney, Agent, or Firm* — Hauptman Ham, LLP

(57) ABSTRACT

A microcirculation detection system including a heating device, a photosensitive array and a processing unit is provided. The heating device is used to heat a skin area. The photosensitive array is used to detect outgoing light from the skin area, and output a plurality of brightness variation signals respectively at different time points within a heating period. The processing unit is used to calculate a change of an array energy distribution varied within the heating period according to the plurality of brightness variation signals to accordingly identify a microcirculation state.

9 Claims, 15 Drawing Sheets

Related U.S. Application Data is a continuation-in-part of application No. 14/955,463, filed on Dec. 1, 2015, now Pat. No. 10,478,080.

(60) Provisional application No. 62/587,114, filed on Nov. 16, 2017.

(51) Int. Cl.
*A61B 5/0295* (2006.01)
*A61B 5/00* (2006.01)
*A61B 5/01* (2006.01)
A61B 5/024 (2006.01)
A61B 5/11 (2006.01)

(52) U.S. Cl.
CPC .......... *A61B 5/4848* (2013.01); *A61B 5/4884* (2013.01); *A61B 5/7235* (2013.01); *A61B 5/742* (2013.01); *A61B 5/02416* (2013.01); *A61B 5/1118* (2013.01); *A61B 2562/046* (2013.01)

(58) Field of Classification Search
CPC ............ A61B 5/7235; A61B 2562/046; A61B 5/02416; A61B 5/1118
See application file for complete search history.

(56) References Cited

U.S. PATENT DOCUMENTS

| | | |
|---|---|---|
| 2009/0247885 A1 | 10/2009 | Suzuki et al. |
| 2011/0137137 A1 | 6/2011 | Shin et al. |
| 2012/0045426 A1 | 2/2012 | St. Cyr et al. |
| 2014/0316286 A1 | 10/2014 | Addison et al. |
| 2015/0164347 A1 | 6/2015 | Pollonini et al. |
| 2015/0269349 A1 | 9/2015 | Taylor et al. |

\* cited by examiner

MICROCIRCULATION DETECTION SYSTEM

RELATED APPLICATIONS

The present application is a continuation-in-part application of U.S. application Ser. No. 15/996,652, filed Jun. 4, 2018, which claims the priority benefit of U.S. Provisional Application Ser. No. 62/587,114, filed on Nov. 16, 2017, and is a continuation-in-part application of U.S. application Ser. No. 14/955,463, filed Dec. 1, 2015, which is based on and claims priority to Taiwan Patent Application Serial Number 104103138, filed Jan. 29, 2015 and Taiwan Patent Application Serial Number 104116752, filed May 25, 2015, the disclosures of which are hereby incorporated by reference herein in their entirety.

BACKGROUND

1. Field of the Disclosure

This disclosure generally relates to the microcirculation detection and, more particularly, to a microcirculation detection system and method that detect a change of the microcirculation with the increasing of a skin surface temperature.

2. Description of the Related Art

Nowadays, portable electronic devices and wearable electronic devices have become the daily necessities to many people. As the lifestyle changes, their functions have also been constantly developed and improved.

At the same time, health has become an important issue among people. Therefore, the portable electronic devices and the wearable electronic devices have also been gradually provided with physiological detection functions to meet the requirements of the users.

SUMMARY

In light of this, the present disclosure provides an array physiological detection system capable of detecting and recording at least three dimensions of physiological characteristics of the user, as well as an operating method thereof.

The present disclosure provides an array physiological detection system which generates a 3D distribution of the physiological characteristics via a plurality of sensing pixels respectively detecting the physiological characteristics of different tissue areas, as well as an operating method thereof.

The present disclosure, provides a microcirculation detection system including a light source, a heating device, a photosensitive array and a processing unit. The light source is configured to irradiate light to illuminate a skin area. The heating device is configured to heat the skin area. The photosensitive array is configured to detect outgoing light from the skin area and output a plurality of PPG signals. The processing unit is configured to convert the plurality of PPG signals to an array energy distribution, identify an arc-like pattern in the array energy distribution, and calculate a frequency variation of an oscillation of the arc-like pattern within a heating period.

The present disclosure further provides a microcirculation detection system including a light source, a heating device, a timer, a photosensitive array and a processing unit. The light source is configured to irradiate light to illuminate a skin area. The heating device is configured to heat the skin area. The timer is configured to count a heating period of the heating device. The photosensitive array is configured to detect outgoing light from the skin area and output a plurality of PPG signals. The processing unit is configured to convert the plurality of PPG signals to an array energy distribution, identify a first arc-like pattern in the array energy distribution at a first time point and a second arc-like pattern in the array energy distribution at a second time point, and identify whether a frequency variation of an oscillation frequency of oscillating between the first arc-like pattern and second arc-like pattern has a peak respectively within a first time interval and a second time interval of the heating period.

The present disclosure further provides a detection method of a microcirculation detection system that includes a light source, a heating device, a photosensitive array and a processing unit. The detection method includes the steps of: lighting a skin area by the light source; heating the skin area by the heating device; detecting, by the photosensitive array, outgoing light from the skin area and outputting a plurality of PPG signals; converting, by the processing unit, the plurality of PPG signals to an array energy distribution; and recognizing, by the processing unit, a frequency variation of an energy fluctuation, within a heating period, at a predetermined position in the array energy distribution, and recognizing two peaks of the frequency variation in two predetermined intervals within the heating period.

In the array physiological detection system and an operating method of said system, a 4D physiological detection system can be further generated by creating a 3D energy variation representative of a change of a 3D energy distribution of the physiological characteristics.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENTS

It should be noted that, wherever possible, the same reference numbers will be used throughout the drawings to refer to the same or like parts.

Figure 1:
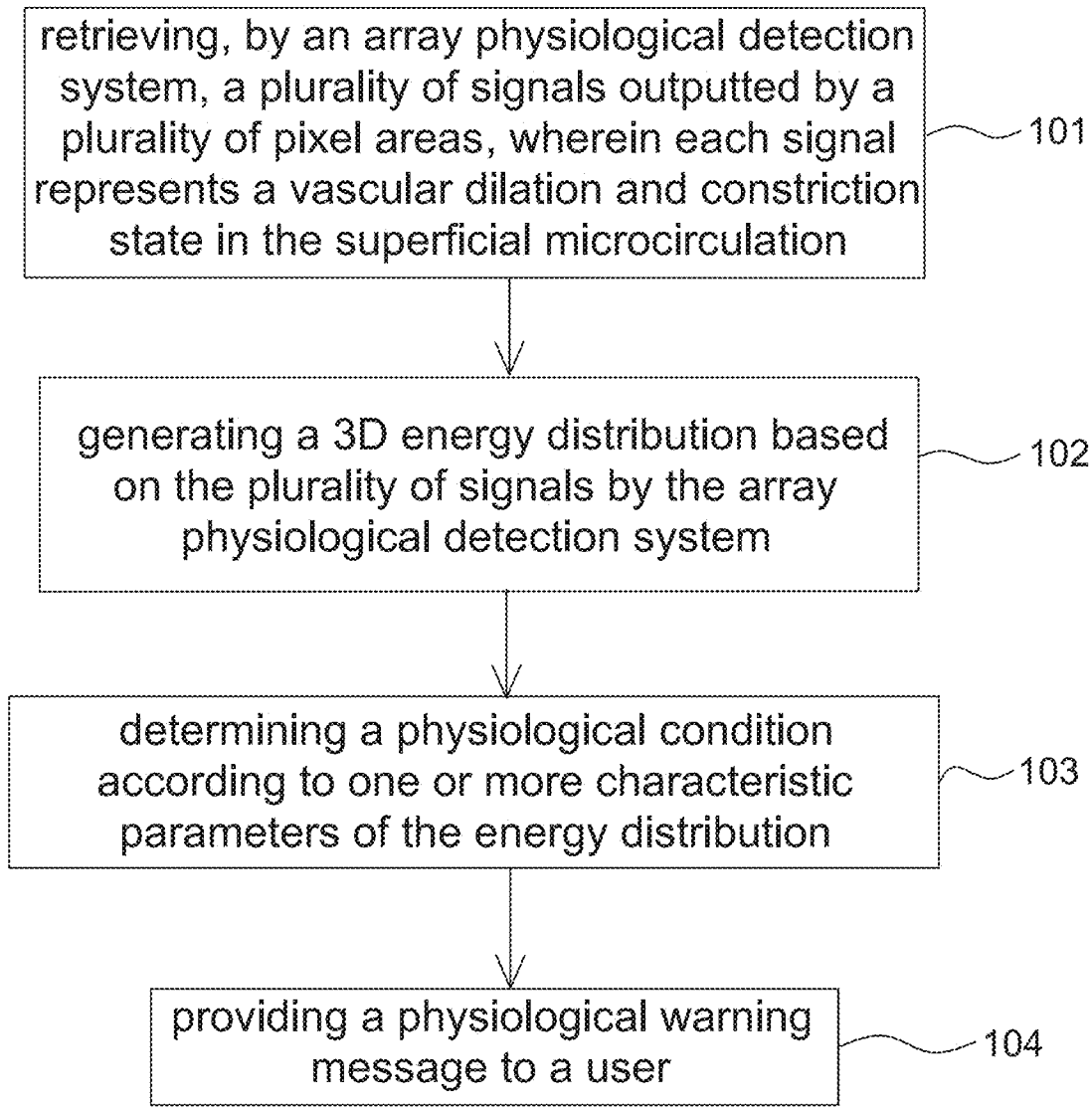
FIG. 1 is a flowchart for detecting a vascular dilation and constriction information in a superficial microcirculation, as performed by an array physiological detection system according to an embodiment of the present disclosure.

FIG. 1 shows a flowchart for detecting the dilation and constriction condition of the blood vessels in a superficial microcirculation, as performed by an array physiological detection system according to an embodiment of the present disclosure. The array physiological detection system detects a 3D energy distribution of a given skin area via the surface of the skin area of a user body part, so as to represent the vascular dilation and constriction condition in the superficial microcirculation. As such, the user will be able to monitor the health condition by himself/herself. In addition, the array physiological detection system according to the embodiment of the present disclosure may be arranged in a portable electronic device or a wearable electronic device to construct a portable physiological detection device. Therefore, a long-term self-supervision mechanism on the health condition is available and suitable for the user. For example, during a long period of time, the portable physiological detection device may monitor a 3D energy variation which is a change of the 3D energy distribution over time (i.e. the variation of the microcirculation information over time). Accordingly, the monitored results of the present array physiological detection system can be combined with the examination results of a short-term physical examination of a medical institution to provide highly reliable physiological information.

First, the array physiological detection system retrieves a plurality of signals outputted by a plurality of pixels. Each signal represents a vascular dilation and constriction state in the superficial microcirculation. The signals are photoplethysmography (PPG) signals as shown in the step 101. In order to obtain the plurality of signals indicative of the vascular dilation and constriction state in the superficial microcirculation, the array physiological detection system needs to obtain the vascular dilation and constriction information in the dermis and uses the information as a microcirculation data. This can be achieved via, for example, an optical detection mechanism where a proper wavelength of light is used such that the light is able to penetrate the epidermis but will not penetrate the dermis when the light is irradiated on the skin. Then, a photosensitive array is used to detect the plurality of signals indicative of the vascular dilation and constriction states in the microcirculation of the skin area. The photosensitive array includes a plurality of photosensitive pixels. Each photosensitive pixel is capable of generating a signal indicative of a vascular dilation and constriction state in the superficial microcirculation. Thus, various statistic values can be obtained for further application.

For instance, the light having a wavelength of 525 nm can be used and the skin penetration depth is smaller than 1 mm. However, different wavelengths of lights can be used for different body parts when detecting the vascular changes in the superficial microcirculation of the dermis. Since the dermis has a depth of about 1 to 3 mm, the wavelength of the light should be properly selected such that the skin penetration depth is not larger than 3 mm, such as 300 to 900 nm.

Next, the array physiological detection system generates a 3D energy distribution based on the plurality of signals indicative of the vascular dilation and constriction state in the superficial microcirculation, as shown in the step 102. The 3D energy distribution refers to a spectral energy distribution. In the step, since the energies of the signals detected by the photosensitive pixels contain various frequencies, a certain frequency can be selected from the various frequencies for further analysis. In an embodiment, the current heartbeat frequency can be calculated from the plurality of signals indicative of the vascular dilation and constriction state in the superficial microcirculation. Then, for a magnitude signal detected by each of the plurality of photosensitive pixels, it can calculate a magnitude variation of the magnitude signal under the heartbeat frequency in order to represent the vascular dilation and constriction state in the superficial microcirculation.

The blood vessels in the superficial microcirculation dilate and constrict as the heart beats. Therefore, for a given photosensitive pixel having a signal, the magnitude of the signal varies more distinctly under the heartbeat frequency or a multiple of the heartbeat frequency than other frequencies other than the heartbeat frequency or the multiple of the heartbeat frequency.

Next, as shown in the step 103, the physiological condition can be determined according to one or more characteristic parameters of the energy distribution, such as the magnitude variation, an average value, the heartbeat frequency . . . etc. It will be described later in the specification on how the physiological characteristics are determined based on the characteristic parameters.

In the following, as shown in the step 104, a physiological warning message can be provided to the user. Accordingly, the user is able to adjust his/his daily schedule and activities.

Figure 2A:
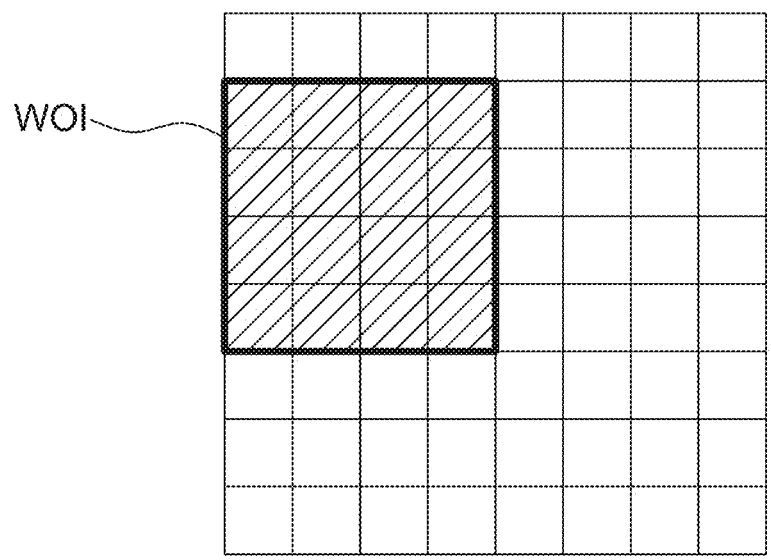
FIG. 2A shows an image frame and a window of interest (WOI) of the image frame as retrieved by the array physiological detection system of an embodiment of the present disclosure.
Figure 2B:
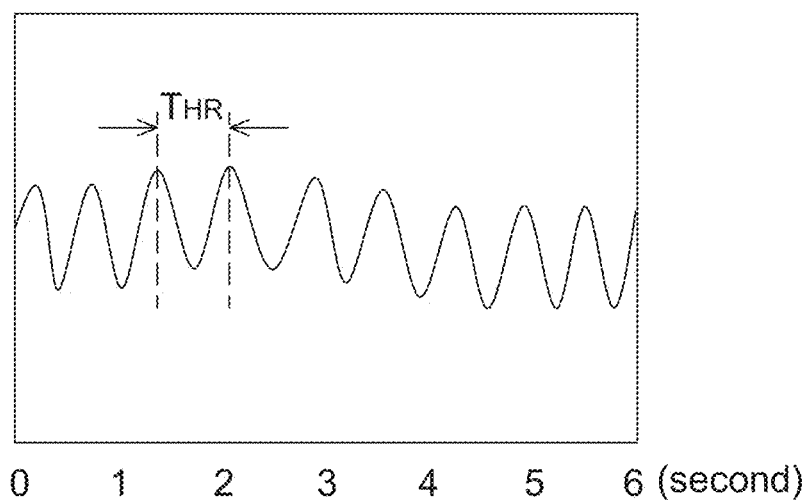
FIG. 2B shows a brightness variation of a plurality of image frames as retrieved by the array physiological detection system of an embodiment of the present disclosure.
Figure 2C:
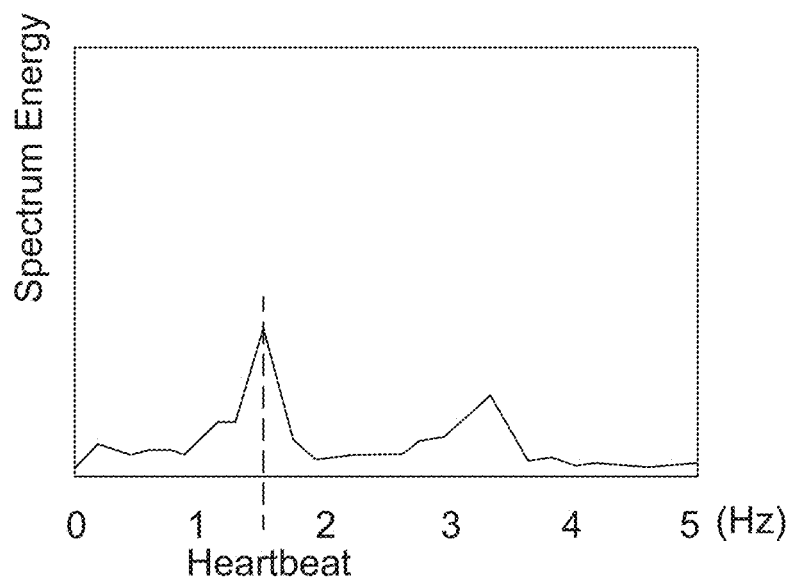
FIG. 2C is a spectrum of a plurality of signals indicative of the vascular dilation and constriction states in the superficial microcirculation, as detected by the array physiological detection system of an embodiment of the present disclosure.
Figure 2D:
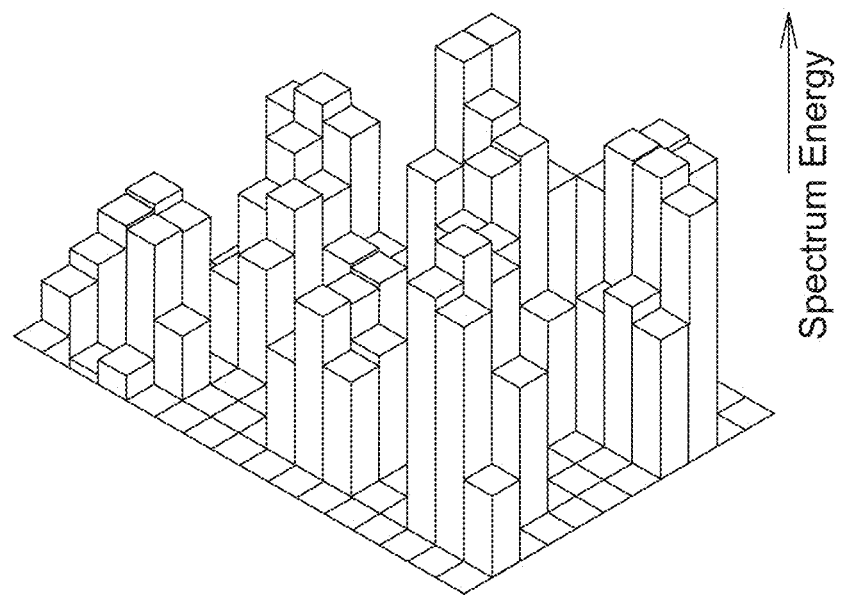
FIG. 2D is an energy distribution diagram of a plurality of pixel areas under a current heartbeat frequency, as detected by the array physiological detection system of art embodiment of the present disclosure.

FIGS. 2A to 2D show a process for detecting the vascular dilation and constriction states in the superficial microcirculation according to the array physiological detection system of the embodiment of the present disclosure. As an example of an optical physiological detection system, FIG. 2A shows a retrieved image frame and a retrieved window of interest (WOI) of the image frame. The size and location of the WOI are adjustable. FIG. 2B shows a brightness variation of a plurality of image frames or the WOIs of the image frames during a period of time, such as 6 seconds, for example. The brightness variation represents the vascular dilation and constriction state in the superficial microcirculation. FIG. 2C shows a spectrum of the plurality of signals indicative of the vascular dilation and constriction state in the superficial microcirculation. The spectrum is obtained by converting the brightness variation of FIG. 2B (namely, the plurality of signals indicative of the vascular dilation and constriction state in the superficial microcirculation) into the frequency domain. The spectrum also shows a current heartbeat frequency. FIG. 2D shows an energy distribution array consisting of a plurality of energy values of a plurality of pixel areas. Namely, the energy distribution array shows a magnitude distribution of the plurality of pixel areas. In FIG. 2D, the height of each bar represents an individual spectral energy under the current heartbeat frequency. It can be observed from FIG. 2D that the detected results (energy values) vary from pixel to pixel, which exhibits a change in the physiological characteristics (such as the distribution or functioning of the capillaries in the dermis), as described later. It should be mentioned that the amplitude of one pixel shown in FIG. 2D is an energy value of one pixel or an average energy value of multiple pixels.

The present disclosure can determine a state of motion according to different microcirculation states. For example, there are four microcirculation states, namely (I) pre-exercise state, (II) warm up completion state, (III) in-exercise state; and(IV) post-exercise cooling state.

Figure 3A:
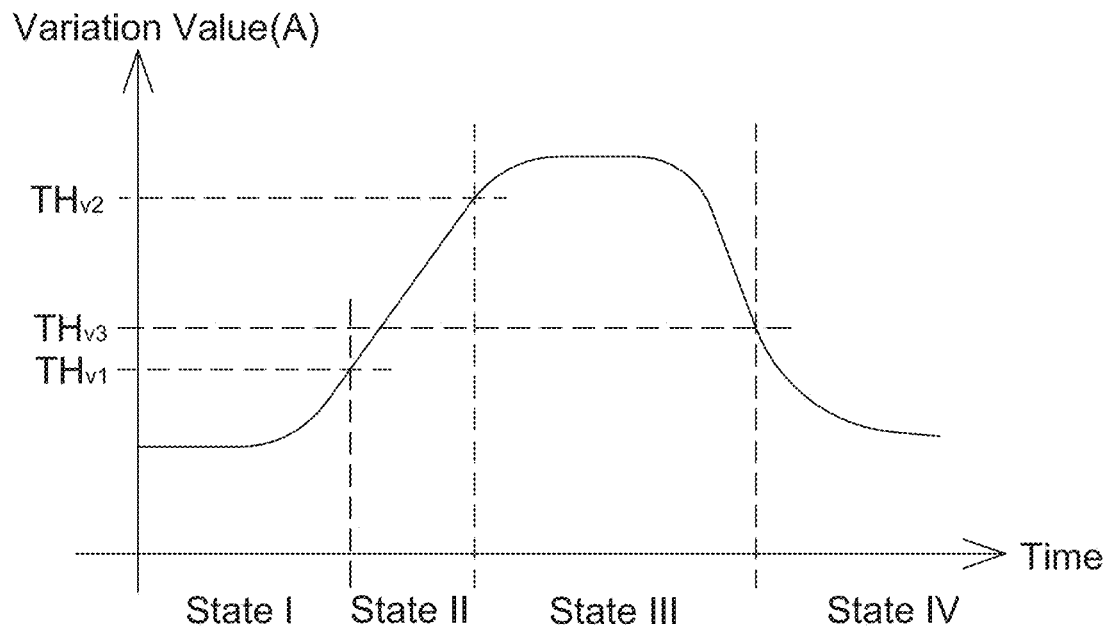
FIG. 3A is a change of a variation value detected by an array physiological detection system of an embodiment of the present disclosure.
Figure 3B:
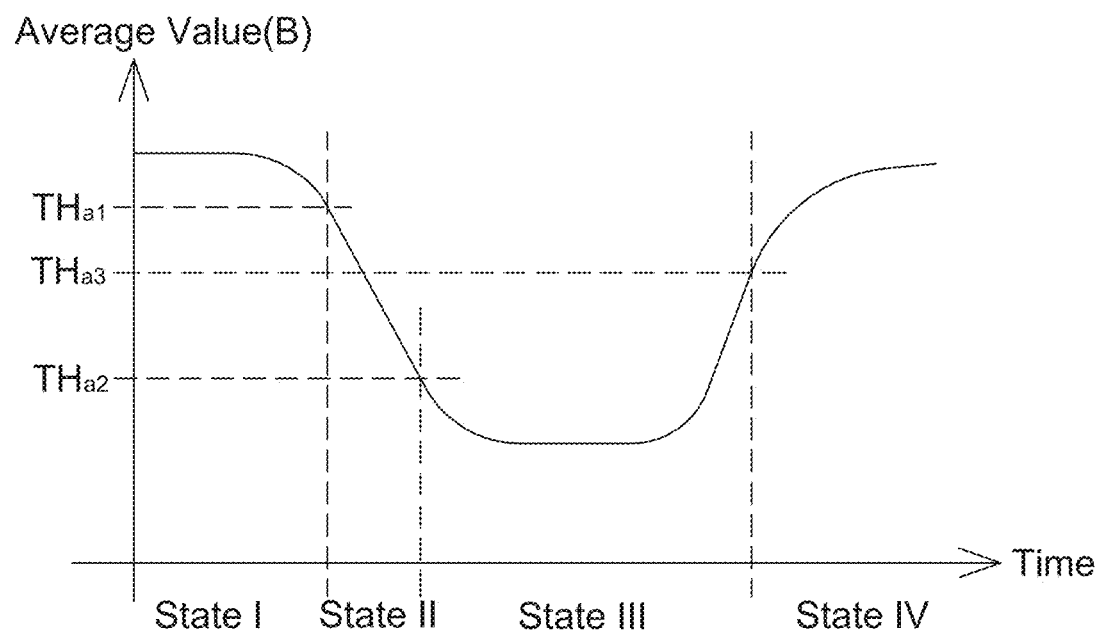
FIG. 3B is a change of an average value detected by an array physiological detection system of an embodiment of the present disclosure.

With reference made to FIGS. 3A and 3B. FIG. 3A is a change of the variation value detected by the array physiological detection system of the embodiment of the present disclosure. FIG. 3B is a change of the average value detected by the array physiological detection system of the embodiment of the present disclosure.

When the user is in the pre-exercise state (I), the magnitude variation (A) of the magnitude signal is not large, but the average value (B) of the magnitude signal is large.

When the user is in the warm up completion state (II), the magnitude variation (A) of the magnitude signal gradually increases, but the average value (B) starts to decrease. When the average value (B) of the magnitude signal is smaller than a warm up average threshold (such as $TH_{a1}$), it indicates that the warm up is completed. Alternatively, if the average value (B) of the magnitude signal is smaller than the warm up average threshold (such as $TH_{a1}$) and the magnitude variation (A) of the magnitude signal is larger than a warm up variation threshold (such as $TH_{v1}$), it indicates that the warm up is completed.

When the user is in the in-exercise state (III), the magnitude variation (A) of the magnitude signal is always large but the average value (B) of the magnitude signal is small. When the average value (B) of the magnitude signal is smaller than an in-exercise average threshold (such as $TH_{a2}$), it indicates that the user is doing the exercise. Alternatively, when the average value (B) of the magnitude signal is smaller than the in-exercise average threshold (such as $TH_{a2}$) and the magnitude variation (A) of the magnitude signal is larger than an in-exercise variation threshold (such as $TH_{v2}$), it indicates that the user is doing the exercise.

When the user is in the post-exercise cooling state (IV), the magnitude variation (A) of the magnitude signal gradually decreases, but the average value (B) of the magnitude signal starts to increase. When the average value (B) of the magnitude signal increases back to a value larger than a cooling average threshold (such as $TH_{a3}$), it indicates that the cooling process is completed. Alternatively, when the average value (B) of the magnitude signal increases back to a value larger than the cooling average threshold (such as $TH_{a3}$) and the magnitude variation (A) of the magnitude signal reduces back to a value smaller than a cooling variation threshold (such as $TH_{v3}$), it indicates that the cooling process is completed.

Although four microcirculation states, three variation thresholds and three average thresholds are shown in FIGS. 3A and 3B, it is noted that the numbers of the microcirculation states, the variation thresholds and the average thresholds are not limited and may be changed according to different applications. Thus, what is shown in FIGS. 3A and 3B is not used to limit the disclosure.

Figure 4:
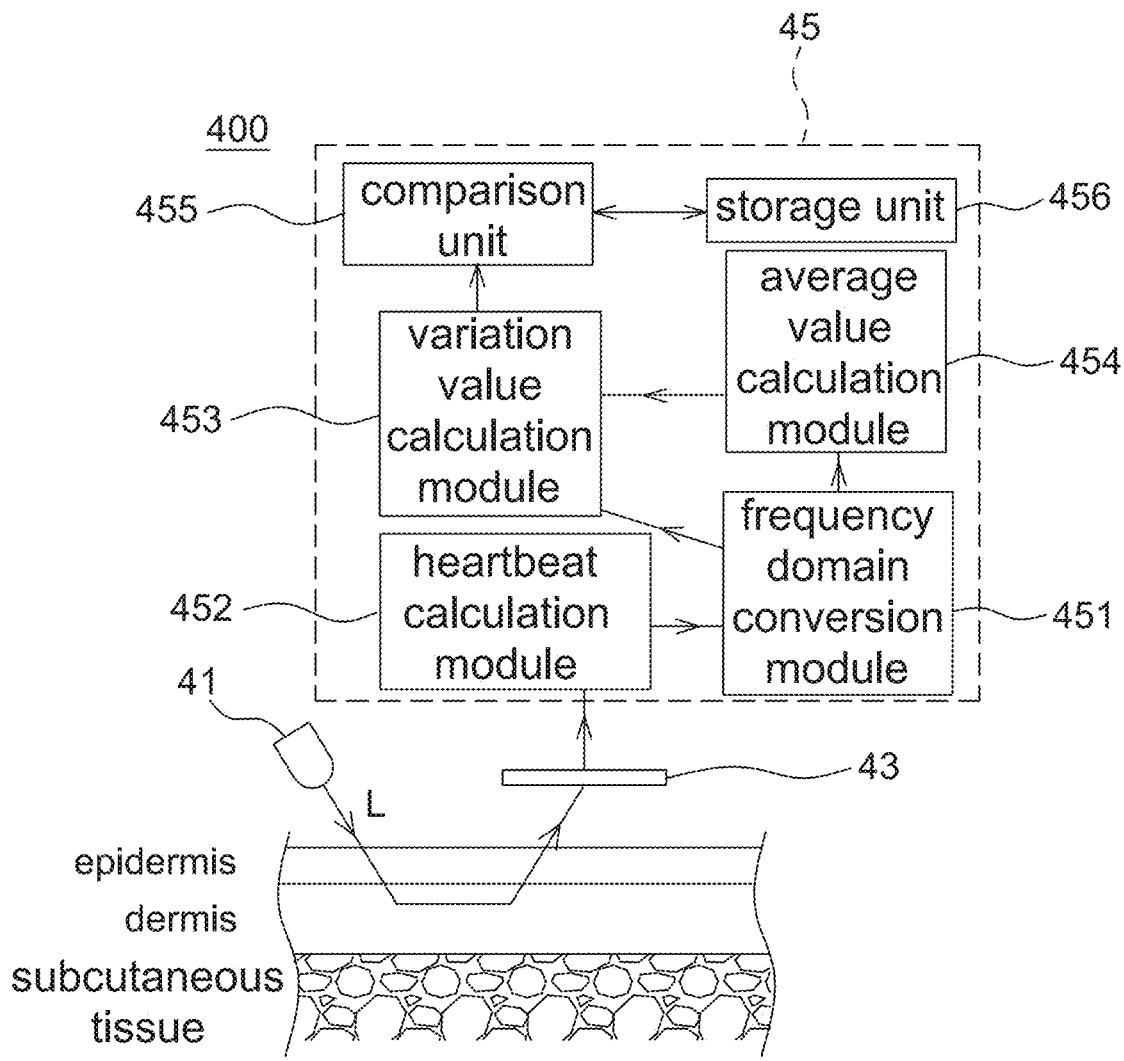
FIG. 4 is a systemic diagram of the array physiological detection system of an embodiment of the present disclosure.

FIG. 4 shows an array physiological detection system 400 according to an embodiment of the present disclosure. The array physiological detection system 400 is used to detect the vascular change in the microcirculation of the skin and includes a light source 41, a photosensitive array 43 and a processing unit 45.

The light source 41 can be a coherent light source, a non-coherent light source or a partial-coherent light source, such as a LED, a laser LED or the like. The light source 41 irradiates the light "L" on a skin area such that the light "L" penetrates the skin and reaches the dermis of the skin. Since the array physiological detection system 400 in the present disclosure simply detects the vascular change in the microcirculation of the dermis without detecting the physiological information of the subcutaneous tissue below the dermis, the light source 41 should have a proper wavelength where the light will not be able to reach the subcutaneous tissue below the derails. The wavelength of the light source 41 is selected as 300 to 940 nm, for example.

In other embodiments, a plurality of light sources can be applied in a light source module, such as light sources with different wavelengths of 525 nm, 880 nm, and 606 nm, to obtain different results of reflected and scattered light from human body. For example, when a short wavelength light source, such as 525 nm, is applied, the result of 3D energy distribution would present as some arc-like pattern in response to physical pressure applied on human body. The arc-like pattern can also be applied to evaluate whether the system is properly wear by the user.

Figure 6A:
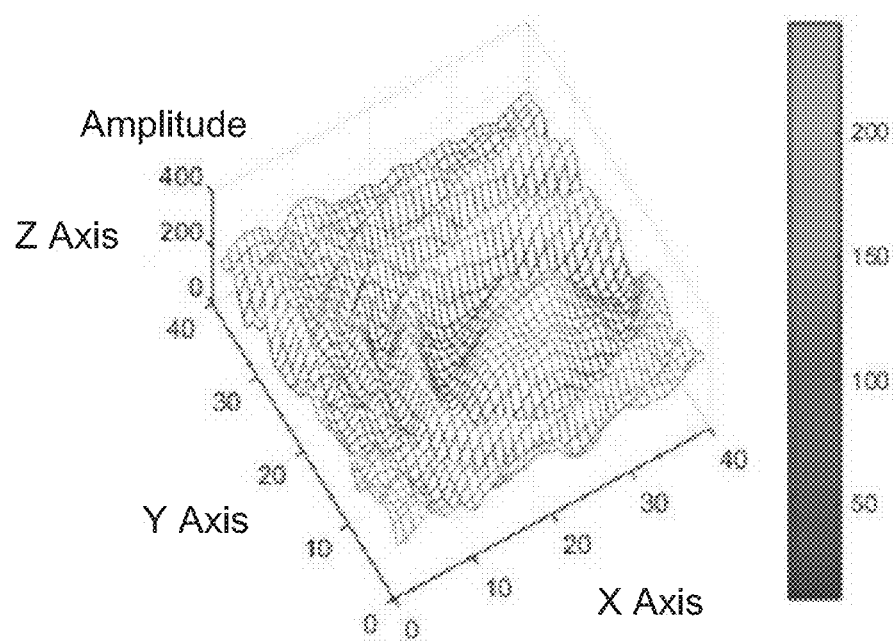
FIGS. 6A and 6B are schematic diagrams of a 3D energy distribution associated with light of 525 nm.
Figure 6B:
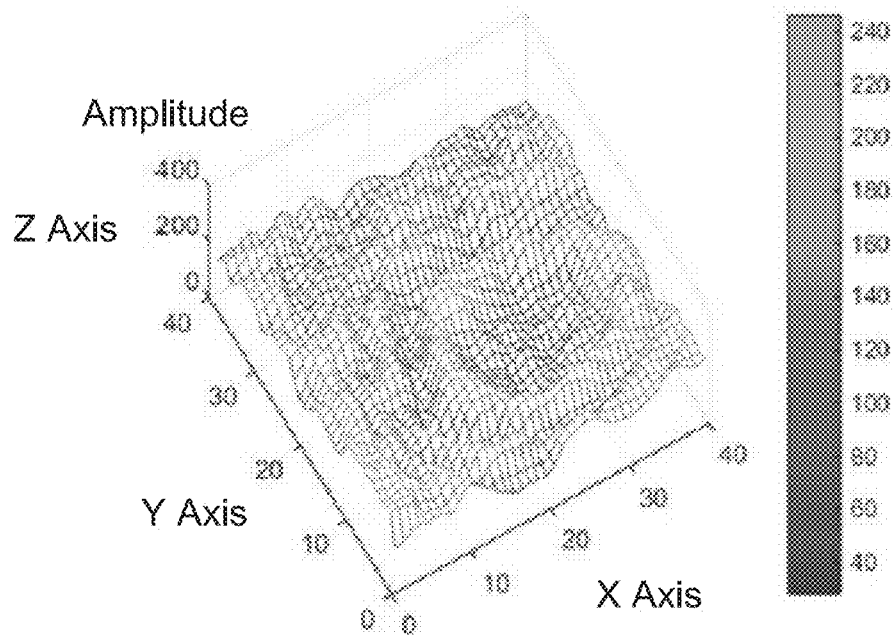
Figure 7A:
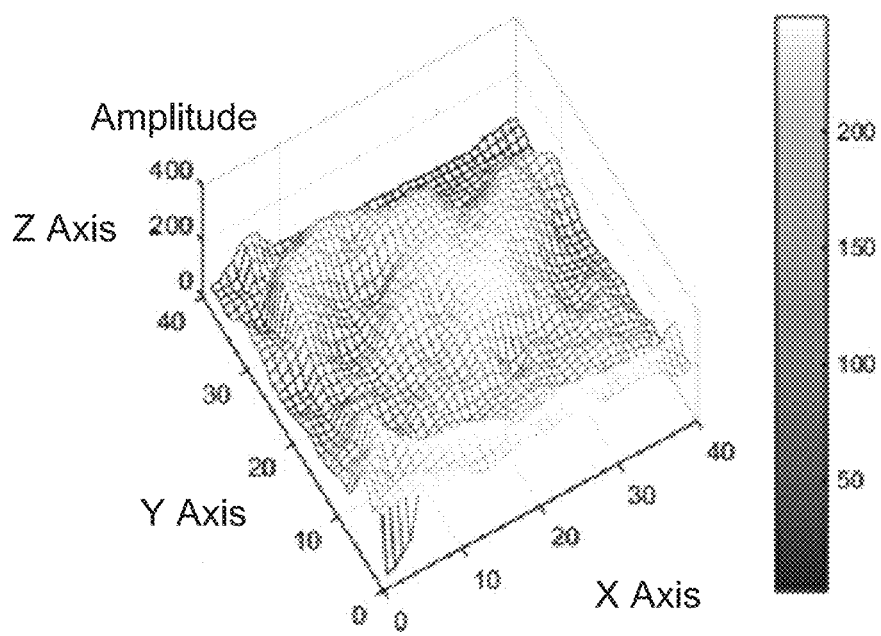
FIGS. 7A and 7B are schematic diagrams of a 3D energy distribution associated with light of 880 nm.
Figure 7B:
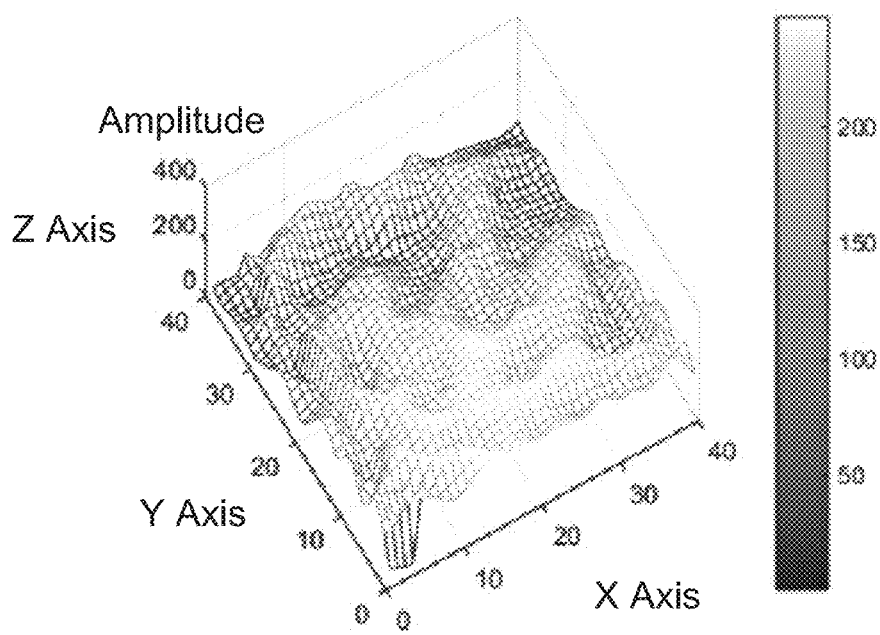

The short wavelength of light source among 300-940 nm can cause more significant absorption variation of human body, and this is presumed to be one reason causing the arc-like pattern as shown in FIGS. 6A and 6B. The long wavelength of light source among 300-940 nm presents high detectable result of 3D energy distribution under high pressure status, thus the system can switch to use different light sources in different situations (e.g., tightly attached or loosely attached) to obtain good quality 3D energy distribution. For example, FIGS. 7A and 7B are schematic diagrams of a 3D energy distribution obtained by emitting light of long wavelength in which no clear arc-like pattern is observed.

The photosensitive array 43 is preferably an active image sensor array such as a CMOS image sensor. Thus, the size and location of the WOI (as shown in FIG. 2A) can be selected as desired according to the sampling result. For instance, the WOI can be determined based on the image quality and the brightness distribution. The photosensitive array 43 cannot output the information detected by the pixels outside of the WOI. The photosensitive array 43 includes the plurality of photosensitive pixels. Each photosensitive pixel is used to continuously detect an outgoing light that emits outwardly from the dermis of the skin area, thereby outputting a plurality of brightness signals as a PPG signal (i.e. the vascular dilation and constriction indication signals in the superficial microcirculation), as shown in FIG. 2A. In some embodiments, the brightness signal is a digital signal, and the photosensitive array 43 can include an analogous-to-digital converter (ADC) for converting analogous signals into digital signals.

The processing unit 45 is configured to convert the brightness signals of the plurality of photosensitive pixels (such as the PPG signal) into a plurality of frequency domain data (as shown in FIG. 2C), thereby obtaining the 3D energy distribution indicative of the vascular dilation and constriction states in the superficial microcirculation (as shown in FIG. 2D). The processing unit 45 also calculates a variation value and an average value of the plurality of frequency domain data and identifies different microcirculation states according to the changes of the variation value and the average value (as shown in FIG. 3B). The processing unit 45 can be any device capable of calculating the data outputted by a sensor array, such as a digital signal processor (DSP), a central processor (CPU) or a microcontroller (MCU).

The processing unit 45 performs the above calculations via software, hardware, firmware or any combination thereof. For example, the processing unit 45 includes a frequency domain conversion module 451, a heartbeat calculation module 452, a variation value calculation module 453, an average value calculation module 454, a comparison unit 455 and a storage unit 456. It is understood that although the various elements in FIG. 4 are directed to different calculation functions, all of the calculation functions are performed by the processing unit 45 since all of the elements are arranged in the processing unit 45. Moreover, the processing unit 45 can also include other calculation functions such as data filtering and amplification. Other insignificant functions of the processing unit 45 are omitted in the specification.

For example, each of the plurality of photosensitive pixels of the photosensitive array 43 outputs a plurality of brightness signals which varies over time and is used as a PPG signal (as shown in FIG. 2B). Thus, the processing unit 45 calculates a heartbeat frequency according to the PPG signals.

In one embodiment, the frequency domain conversion module 451 converts the PPG signal (as shown in FIG. 2B) of each of the plurality of photosensitive pixels into a frequency domain data (as shown in FIG. 2C). The heartbeat calculation module 452 calculates an estimated heartbeat frequency according to the frequency domain data of each of the plurality of photosensitive pixels. Among the estimated heartbeat frequencies of the plurality of photosensitive pixels, the one with the highest statistic will be used as the heartbeat frequency. Namely, an estimated heartbeat frequency can be calculated for each of the plurality of photosensitive pixels. Thus, a plurality of heartbeat frequencies will be calculated for all of the photosensitive pixels. Among the plurality of heartbeat frequencies, the one that corresponds to the largest number of the pixels will be used as the heartbeat frequency. In this manner, it is able to reduce the error resulting from the noise and to improve the calculation accuracy.

The plurality of photosensitive pixels in an image frame (or in the WOI of the image frame) has a plurality of brightness signals outputted by the photosensitive array 43. Thus, in another embodiment, all or a part of the plurality of brightness signals in each image frame (or in the WOI of the image frame) may be added by the processing unit 45 to calculate a sum of brightness. As a result, the plurality of image frames will have a plurality of sums of brightness.

The heartbeat frequency may be calculated based on the plurality of sums of brightness. Namely, in this embodiment, the processing unit 45 calculates a sum of brightness for each of the plurality of image frames. For the plurality of image frames, the processing unit 45 calculates a variation of the sum of brightness, which is used as a PPG signal as shown in FIG. 2B. In this embodiment, the heartbeat calculation module 452 can calculate the heartbeat frequency in the time domain. For example, as shown in FIG. 2B, the heartbeat calculation module 452 calculates a reciprocal of a time internal THR. Alternatively, the variation of the sum of brightness may be converted into the frequency domain by the heartbeat calculation module 452 first, so as to generate a frequency domain data as shown in FIG. 2C. Then, the heartbeat calculation module 452 calculates the heartbeat frequency based on the frequency domain data. The heartbeat frequency is the one with the largest spectral energy shown in FIG. 2C. In other words, in this embodiment, FIG. 2B represents the variation of brightness for a single photosensitive pixel. FIG. 2B also represents a variation of the sum of brightness for the plurality of image frames. For a single photosensitive pixel having a variation of brightness, FIG. 2C can represent a frequency domain data of the variation of brightness thereof. For the plurality of image frames having a variation of the sum of brightness, FIG. 2C can represent a frequency domain data of the variation of the sum of brightness thereof. This is dependent on the application. In the present disclosure, a proper algorithm such as fast Fourier transform (FFT) may be used to perform the time to frequency domain conversion. However, this is not used to limit the present disclosure.

Upon the determination of the heartbeat frequency, for each of the plurality of photosensitive pixels, the variation value calculation module 453 may generate a spectral energy value under the heartbeat frequency. As such, the 3D energy distribution (or an energy set) can be formed, as shown in FIG. 2D. The variation value calculation module 453 calculates an energy variation of the 3D energy distribution (or the energy set) which represents a magnitude variation. For example, an energy difference between two adjacent photosensitive pixels may be calculated, and the energy differences of all of the photosensitive pixels may be added to generate a sum of energy difference. Alternatively, for each photosensitive pixel having a respective energy value, an energy difference between the respective energy value of the photosensitive pixel and an average energy may be calculated. Then, the energy differences (associated with the average energy) of all of the photosensitive pixels may be added to generate a sum of energy difference (associated with the average energy). Still alternatively, a variance of the energy set can be calculated. However, the calculations of the variation value calculation module 453 are not limited to the above as long as the calculation module 453 is able to obtain the variation of the 3D energy distribution (or the energy set). In this embodiment, the variation value of the 3D energy distribution is a variation of the spectral energy under the heartbeat frequency.

After the heartbeat frequency is determined, the average value calculation module 454 generates a spectral energy value under the heartbeat frequency for each of the plurality of photosensitive pixels. As such, the 3D energy distribution (or 3D energy set) can be formed, as shown in FIG. 2D. The average value calculation module 454 calculates an average value of the 3D energy distribution (or 3D energy set) which represents a magnitude average value. In the embodiment, the average value is an average value of the spectral energy under the heartbeat frequency.

The 3D energy distribution as shown in FIG. 2D can be applied to calculate and generate a representative position for later evaluation. For example, the distribution values higher than a threshold value can be used to calculate a position of center of mass, a position of centroid, or a center position of the used distribution values. The representative position would vary according to physiologic status of user, wherein the physiologic status is related to physical motion or mental change of user.

It is noted that although the 3D energy distribution (or 3D energy set) are calculated by the variation value calculation module 453 and the average value calculation module 454 in the above embodiment, the 3D energy distribution (or 3D energy set) can also be calculated by other components in the processing unit 45 such as the frequency domain conversion module 451 or the heartbeat calculation module 452.

In some embodiments, the processing unit 45 can also identify different microcirculation states based on a heartbeat frequency in addition to the changes of the variation value and the average value. Namely, in the specification, the processing unit 45 can identify different microcirculation states (such as the pre-exercise state, the warm up completion state, the in-exercise state and the post-exercise cooling state) based on any combination between the change of the variation value, the change of the average value, and the change of the heartbeat frequency. However, the microcirculation states are not limited to the above.

The comparison unit 455 can identify different microcirculation states by comparing the variation value with at least one variation threshold (such as $TH_{v1}$ to $TH_{v3}$ in FIG. 3A). The comparison unit 455 can also identify different microcirculation states by comparing the average value with at least one average threshold (such as $TH_{a1}$ to $TH_{a3}$ in FIG. 3B). In addition, the comparison unit 455 can identify different microcirculation states by comparing the heartbeat frequency with at least one heartbeat threshold. All of the above thresholds can be stored in the storage unit 456, which can be a conventional memory (but is not limited thereto).

Figure 5:
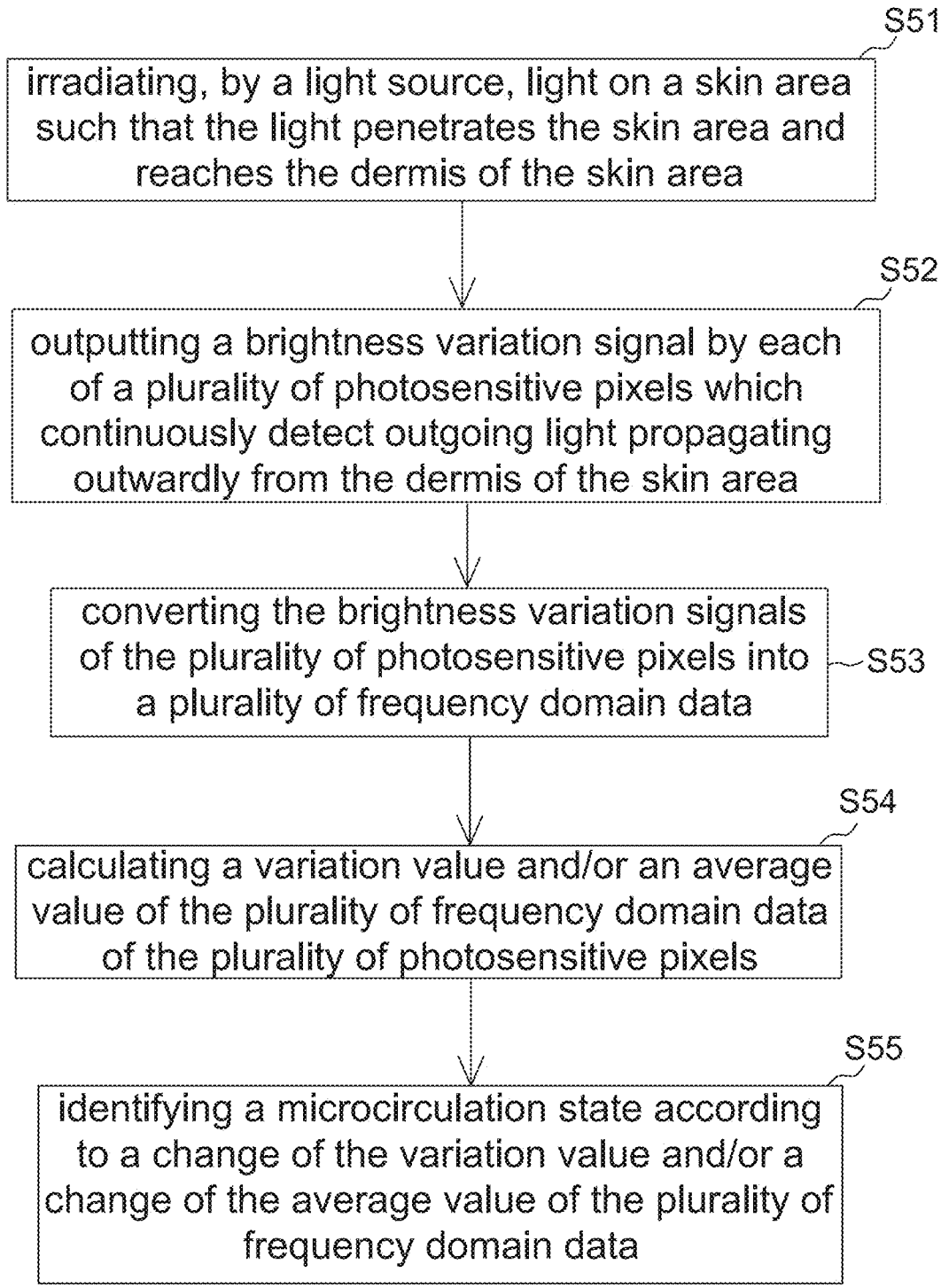
FIG. 5 is a flowchart of an operating method of the array physiological detection system of an embodiment of the present disclosure.

FIG. 5 shows a flowchart of an operating method of the array physiological detection system of the embodiment of the present disclosure, which is performed to detect the change of skin microcirculation via a plurality of photosensitive pixels. The operating method includes irradiating the light of a light source on a skin area such that the light of the light source penetrates the skin and reaches the dermis of the skin (S51), outputting a brightness variation signal by each of the plurality of photosensitive pixels continuously detecting the outgoing light that emits outwardly from the dermis of the skin area (S52), converting the brightness variation signals of the plurality of photosensitive pixels into a plurality of frequency domain data (S53), calculating a variation value and/or an average value of the plurality of frequency domain data of the plurality of photosensitive pixels (S54), and identifying a microcirculation state according to a change of the variation value and/or a change of the average value of the plurality of frequency domain data (S55).

The operating method of the embodiment of the present disclosure is described below with reference made to FIGS. 2A to 2D, 3A to 3B and 4-5.

In the step S51, the light source 41 irradiates the light "L" on the skin area so that the light "L" penetrates the surface of the skin area and reaches the dermis of the skin area. As stated above, the wavelength of the light "L" should be properly selected such that the light "L" does not penetrate the dermis of the skin. As such, the plurality of photosensitive pixels simply detects the vascular change in the superficial microcirculation without detecting the physiological information of the subcutaneous tissue below the dermis.

In the step S52, each of the plurality of photosensitive pixels of the photosensitive array 43 continuously detects the outgoing light that emits outwardly of the dermis of the skin area and respectively outputs a brightness variation signal, as the PPG signal in FIG. 2B. Therefore, the quantity of the PPG signals outputted by the photosensitive array 43 is the same as the quantity of the active pixels.

In the step S53, the processing unit 45 converts the brightness variation signals of the plurality of photosensitive pixels into a plurality of frequency domain data, as shown in FIG. 2C. Therefore, the quantity of the plurality of frequency domain data is also the same as the quantity of the active pixels.

In the step S54, the processing unit 45 calculates a variation value and/or an average value of the plurality of frequency domain data of the plurality of photosensitive pixels (S54). Since the characteristics of the plurality of frequency domain data are more noticeable under the heartbeat frequency or a multiple of the heartbeat frequency, the processing unit 45 calculates a heartbeat frequency according to the brightness variation signals of the plurality of photosensitive pixels prior to the calculations of the variation value and/or the average value. As stated above, the heartbeat frequency may be directly calculated in the time domain or may be calculated in a different manner in the frequency domain. Then, the 3D energy distribution (or the energy set) under the heartbeat frequency can be generated as shown in FIG. 2D. Next, based on the 3D energy distribution (or the energy set), the processing unit 45 can calculate an average value and/or a variation value of the spectral energy under the heartbeat frequency. The calculation of the variation value is not described herein as it has been discussed previously.

In the step S55, the processing unit 45 can identify a microcirculation state according to the change(s) of the variation value and/or the average value over time. The identification is carried out by comparing the variation value with at least one variation threshold and/or by comparing the average value with at least one average threshold (as shown in FIGS. 3A and 3B).

As stated above, in some embodiments, the processing unit 45 can also identify a microcirculation state based on the above factors along with the change of the heartbeat frequency over time.

Finally, the processing unit 45 notifies the user of the detected microcirculation state through images, sound or the like. However, this is not taken as a limited sense.

In summary, the present disclosure does not determine the state of motion via the percent of Maximal Heart Rate (MHR) or the user's own judgement. Instead, the state of motion is determined according to the vascular change in the superficial microcirculation associated with the blood circulation and distribution. In this mechanism, the vascular change in the superficial microcirculation of the skin can be represented by a plurality of brightness signals generated by the plurality of photosensitive pixels of the photosensitive array continuously detecting the outgoing lights that emit outwardly of the dermis. The plurality of brightness signals may form a PPG signal.

As stated above, the processing unit 45 can determine that the user is in the warm up completion state when the average value is smaller than a warm up average threshold (such as $TH_{a1}$) and/or when the magnitude variation (A) is larger than a warm up variation threshold (such as $TH_{v1}$). Further-more, the processing unit 45 determines that the user is doing the exercise when the average value reduces back to a value smaller than an in-exercise average threshold (such as $TH_{a2}$) and/or when the magnitude variation (A) is larger than an in-exercise variation threshold (such as $TH_{v2}$). Moreover, the processing unit 45 determines that the user is in the post-exercise cooling state when the average value increases back to a value larger than a cooling average threshold (such as $TH_{a3}$) and/or when the magnitude variation (A) reduces back to a value smaller than a cooling variation threshold (such as $TH_{v3}$). The determination on the state of the motion in regard to the thresholds may vary according to the application.

In an alternative embodiment, a physiological detection device, e.g., 400 shown in FIG. 4, of the present disclosure is further used to confirm whether the physiological detection device is well-attached with a skin surface to allow the physiological detection device to operate normally. It is known that the relative movement between a skin surface and the physiological detection device can degrade the image quality of the detected signal. Accordingly, to confirm an attaching status is important.

For example referring to FIG. 4, the physiological detection device 400 of this embodiment includes a light source module 41, a photosensitive array 43 and a processing unit 45. In addition, the physiological detection device 400 of this embodiment further includes a display 47 (e.g., shown in FIG. 9) used to show a detected result of the physiological detection device, e.g., alerting message, indication message or the like.

In this embodiment, the light source module 41 is used to irradiate light of different wavelengths on a tissue area below a skin to detect different depths of the tissue area. As mentioned above, a shorter wavelength herein is used to confirm whether a well-attached status is formed. For example, the light source module 41 irradiates light of a first wavelength, e.g., between 500 nm and 550 nm, on the tissue area to be measured.

The photosensitive array 43 is used to detect outgoing light from the tissue area and output a plurality of PPG signals each shown as FIG. 2B. As mentioned above, one pixel outputs one PPG signal, or a plurality of pixels outputs one averaged PPG signal, e.g., added by hardware circuit, as shown in FIG. 2B.

The processing unit 45 is used to convert the plurality of PPG signals to a 3D energy distribution, e.g., shown in FIG. 2D, identify an arc-like pattern in the 3D energy distribution, and control the display 47 to show a message indicating that the physiological detection device 41 is ready (i.e. well-attached) when the arc-like pattern is confirmed, e.g., as shown in FIGS. 6A and 6B. The method of generating the 3D energy distribution has been illustrated above.

In one non-limiting embodiment, the arc-like pattern includes at least one ring formed by energy amplitudes in the 3D energy distribution larger than an energy threshold, e.g., peaks with lighter color in FIGS. 6A and 6B. It is seen from FIGS. 6A and 6B that more than one ring is shown. The processing unit 45 obtains the ring in other way, e.g., calculating a difference between energy amplitudes of adjacent pixels and finding local maximums in the 3D energy distribution.

However, if an arc-like pattern does not exist in the 3D energy distribution, it means that the physiological detection device 400 might not be worn properly or tight enough for the physiological detection. Accordingly, the processing unit 45 is further used to control the display 47 to show a message of changing a location of the physiological detection device 400 or changing an attaching status of the physiological detection device 400 when no arc-like pattern is confirmed. The physiological detection device 400 is arranged in a way that an alert message is provided to the user till the arc-like pattern is detected. After the arc-like pattern is confirmed, the 3D energy distribution detected by the physiological detection device 400 is considered as containing valid data.

As mentioned above, the physiological detection device 400 of the present disclosure is able to detect the superficial microcirculation at different tissue depths. For example, the processing unit 45 is further used to control the light source module 41 to irradiate light of a second wavelength, which is longer than the first wavelength, to cause the photosensitive array 43 to detect the outgoing light from a different tissue depth after said arc-like pattern is confirmed. In one non-limiting embodiment, the second wavelength is between 850 nm and 900 nm or between 590 nm and 620 nm, but not limited thereto. By changing the wavelength of light and analyzing different 3D energy distributions corresponding to different light wavelengths, it is possible to obtain more detailed information within a detected tissue area. In one non-limiting embodiments, the processing unit 45 is arranged to control the display 47 to show a message of changing the light wavelength to obtain a suitable 3D energy distribution.

For example, FIGS. 7A and 7B are schematic diagrams of 3D energy distribution corresponding to the light source module 41 irradiating light of 880 nm, and using a photosensitive array with 480*480 pixels each having a size of 5 μm*5 μm. It is seen from FIGS. 7A and 7B that no clear arc-like pattern is shown. This is because when the light having a longer wavelength is adopted, the irradiated light penetrates more tissues (including shallower and deeper tissues) and thus more complicated data is reflected in the detected 3D energy distribution. More complicated process is required to analyze the detected 3D energy distribution associated with the light of a longer wavelength. Accordingly, in one non-limiting embodiment, the processing unit 45 is not used to identify the arc-like pattern in the 3D energy distribution associated with the light of the second wavelength for simplification. That is, in the present disclosure, the processing unit 45 is arranged to confirm whether the physiological detection device 400 is worn properly according to the light of a shorter wavelength, e.g., the first wavelength mentioned herein, but not to confirm the wearing status using the light of a longer wavelength, e.g., the second wavelength mentioned herein.

In addition, the processing unit 45 is further used to control the display 47 to show a message indicating a direction of moving the physiological detection device 400 to obtain more meaningful data. FIGS. 7A and 7B are the 3D energy distribution detected by the photosensitive array 43 at different time points using a same light wavelength. The 3D energy distribution repeatedly changes between FIGS. 7A and 7B with time. It is seen that amplitudes at lower Y-Axis section (about at Y=0-10) always have higher energy without changing with time, and this is considered that the detected data exceeds a detectable range of the system. According, the processing unit 45 informs the user by showing on the display 47 to move the physiological detection device 400 along a positive Y-Axis (e.g., Y=40) in order not to detect the always-high amplitude area.

In other embodiments, the processing unit 45 calculates a position of center of mass, a position of centroid, or a center position of the 3D energy distribution. If the calculated position is not at a center of the 3D energy distribution, the processing unit 45 controls the display 47 to direct a user to move the physiological detection device 400 to cause said position to be close to the center of the 3D energy distribution. That is, the processing unit 45 is arranged to control the display 47 to show a direction of moving the physiological detection device 400 to a predefined area, e.g., an area having more vessels.

In the above embodiment, when the physiological detection device 400 is not worn properly, the physiological detection device 400 informs the user to change a location or to wear the device with different tightness.

Figure 8:
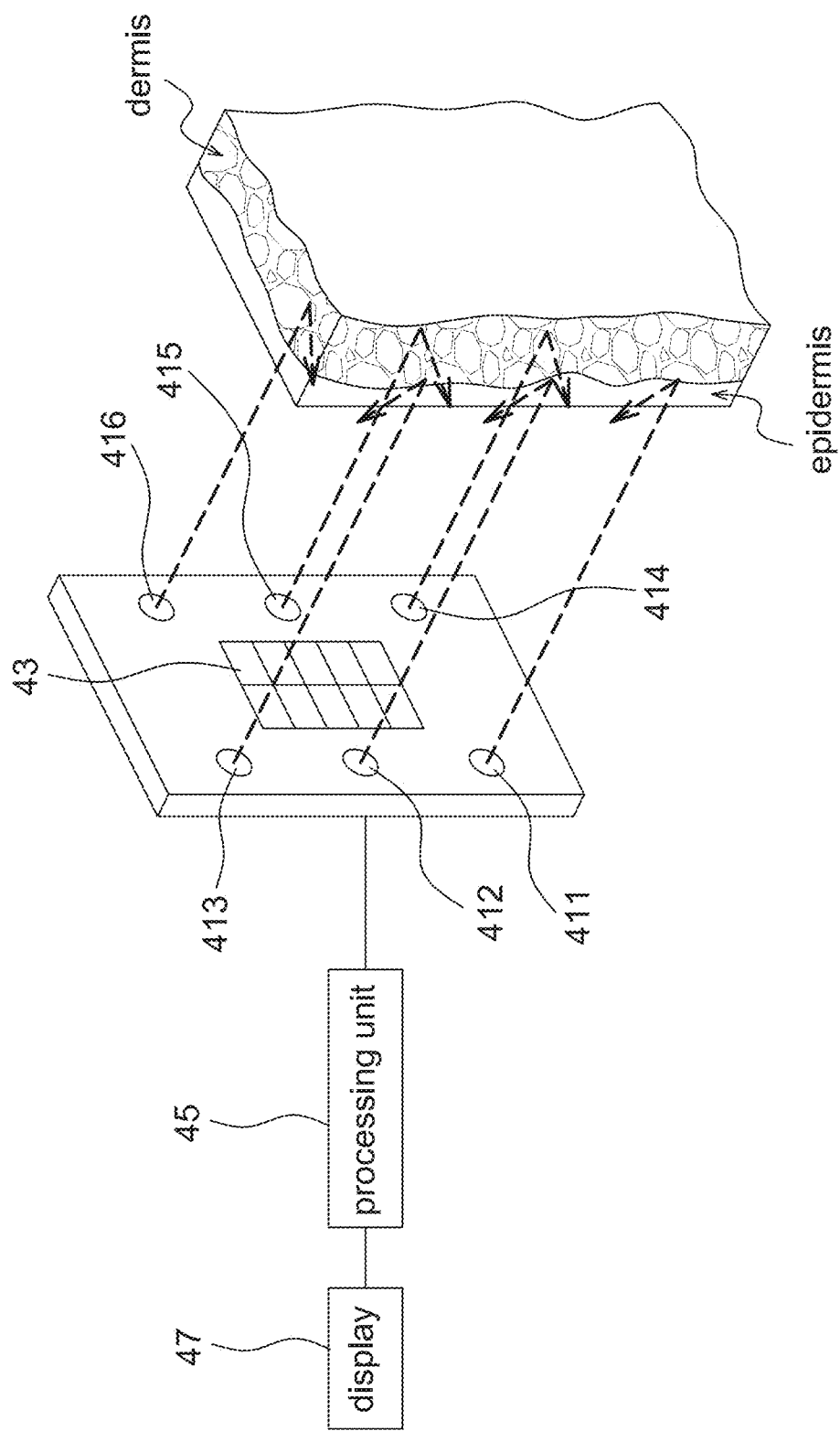
FIG. 8 is a schematic diagram of a photosensitive detection device according to another embodiment of the present disclosure.

In an alternative embodiment, the physiological detection device 400 performs a self-adjustment at first, and if the self-adjustment cannot fulfill the requirement, e.g., detecting an arc-like pattern, then informs the user to adjust the location or tightness as mentioned above. Referring to FIG. 8, it is a schematic diagram of a physiological detection device 400 according to an alternative embodiment of the present disclosure which also includes a light source module, a photosensitive array 43 and a processing unit 45. In the present embodiment, the physiological detection device 400 also includes a display 47.

The light source module in the present embodiment includes a plurality of light emitting diodes (LED), e.g., LEDs 411-416 shown in FIG. 8, used to irradiate light of a first wavelength on a tissue area with different groups of light emitting diodes among the plurality of light emitting diodes, wherein the first wavelength is between 500 nm and 550 nm. For example, the first group includes the light emitting diodes 411-413. It should be mentioned that a number of the LEDs and a size of the photosensitive array are not limited to those shown in FIG. 8.

The photosensitive array 43 is used to detect outgoing light from the tissue area and output a plurality of PPG signals, e.g., each shown as FIG. 2B. It should be mentioned that an arrangement between the photosensitive array 43 and the multiple LEDs 411-416 is not limited to that shown in FIG. 8 as long as the photosensitive array 43 detects outgoing light from different directions when different groups of LEDs are lighted.

The processing unit 45 is used to convert the plurality of PPG signals to a 3D energy distribution, identify an arc-like pattern in the 3D energy distribution obtained from lighting a first group of light emitting diodes, and control a second group of light emitting diodes, e.g., LEDs 414-416, to emit light when the arc-like pattern is not confirmed in the 3D energy distribution. Details of the arc-like pattern have been described above and thus are not repeated herein.

The difference from the above embodiment is that when the arc-like pattern is not confirmed in the 3D energy distribution associated with the first group of LEDs, the processing unit 45 changes another group of LEDs to irradiate the tissue area, also using the light of a first wavelength. In addition to change LEDs at different locations to irradiate light, the processing unit 45 further changes a window of interest (e.g., WOI shown in FIG. 2A) in an image frame retrieved by the photosensitive array 43 in order to obtain a suitable 3D energy distribution. If an arc-like pattern is detectable by the self-adjustment, e.g., lighting different LEDs or changing WOI, the processing unit 45 does not control the display 47 to show a message for a manual adjustment.

As mentioned above, if the self-adjustment is work, the physiological detection device 400 can be used to detect the superficial microcirculation at different tissue depths. That is, the processing unit 45 is further used to control the light source module to irradiate light of a second wavelength, which is longer than the first wavelength, when an arc-like pattern is confirmed in the 3D energy distribution associated with first group of light emitting diodes. As mentioned above, the second wavelength is selected between 850 nm and 900 nm or between 590 nm and 620 nm, but not limited thereto.

In an alternative embodiment, a physiological detection system includes two physiological detection device, e.g., referred to array PPG detectors, for monitoring the superficial microcirculation at different parts of a human body. For example referring to FIG. 9, it is a block diagram of a physiological detection system 500 according to an alternative embodiment of the present disclosure.

Figure 9:
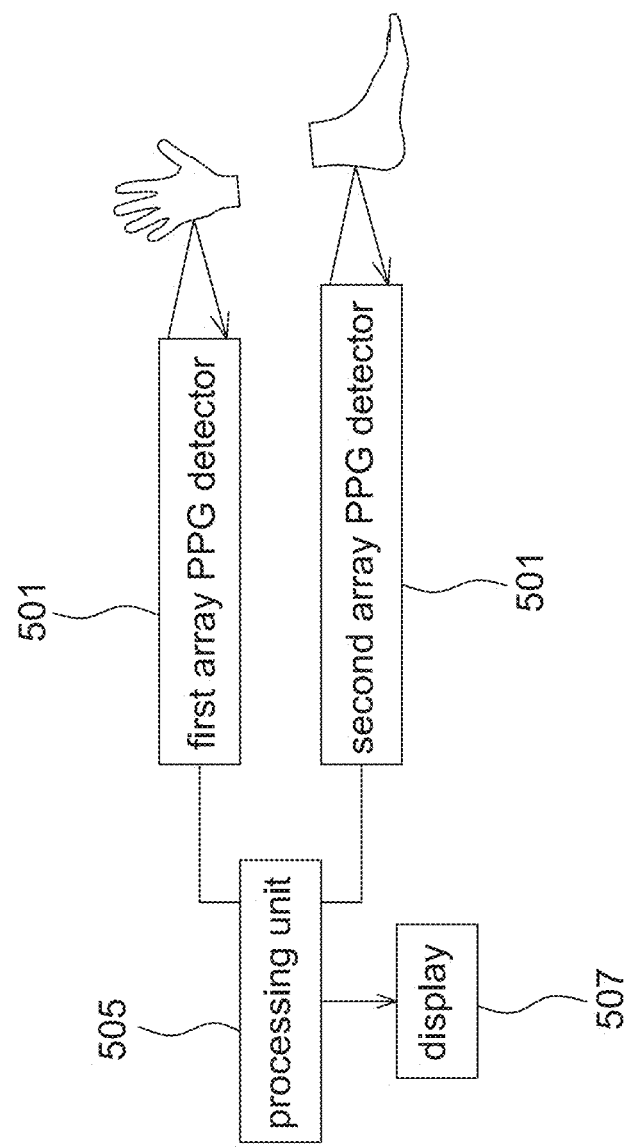
FIG. 9 is a block diagram of a photosensitive detection system according to an alternative embodiment of the present disclosure.

The physiological detection system 500 includes a first array PPG detector 501, a second array PPG detector 503, a processing unit 505 and a display 507. It should be mentioned that although FIG. 9 shows that the processing unit 505 is arranged outside of the first array PPG detector 501 and the second array PPG detector 502, the present disclosure is not limited thereto. In one non-limiting embodiment, the processing unit 505 is integrated in the first array PPG detector 501 or the second array PPG detector 503.

The first array PPG detector 501 and the second array PPG detector 503 are similar to the photosensitive array 43 shown in FIG. 4. In this embodiment, the first array PPG detector 501 is used to generate a plurality of first PPG signals, and the second array PPG detector 503 is used to generate a plurality of second PPG signals. The method of a photosensitive array generating a plurality of PPG signals (as shown in FIG. 2B) has been illustrated above.

For example, the first array PPG detector 501 includes a first light source module and a first photosensitive array. The first light source module is used to irradiate light of a first wavelength on a first tissue area. The first photosensitive array is used to detect outgoing light from the first tissue area and output the plurality of first PPG signals. The second array PPG detector includes a second light source module and a second photosensitive array. The second light source module is used to irradiate light of the first wavelength on a second tissue area. The second photosensitive array is used to detect outgoing light from the second tissue area and output the plurality of second PPG signals. For example, the first wavelength is between 500 nm and 550 nm.

The display 507 is also used to show a detected result of the physiological detection system.

The processing unit 505 uses a similar method mentioned above to convert the plurality of first PPG signals and the plurality of second PPG signals to a first 3D energy distribution and a second 3D energy distribution, respectively. In this embodiment, the first tissue area is at a hand of a user and the second tissue area is at a leg of the user without particular limitations as long as the two array PPG detectors are located at two different skin surfaces to be measured. For example, the processing unit 505 compares the first 3D energy distribution and the second 3D energy distribution to determine whether the superficial microcirculation at hand or a leg becomes worse, e.g., due to at a sitting posture for a long time. Similarly, before the comparison, the processing unit 505 confirms whether the first array PPG detector 501 and the second PPG detector 502 are worn properly. That is, the processing unit 505 identifies an arc-like pattern in the first 3D energy distribution and the second 3D energy distribution. The physiological detection system 500 operates normally when both the first 3D energy distribution and the second 3D energy distribution contain a detectable arc-like pattern, respectively.

After the arc-like pattern is confirmed in both the first 3D energy distribution and the second 3D energy distribution, the physiological detection system 500 continuously monitors variations of the first 3D energy distribution and the second 3D energy distribution with time.

In one embodiment, the processing unit 505 calculates a first average energy of the first 3D energy distribution and a second average energy of the second 3D energy distribution, respectively. The processing unit 505 further calculates a ratio of or a difference between the first average energy and the second average energy, and monitors a variation of the ratio or the difference. When the ratio or the difference changes to exceed to a variation threshold, it means that the superficial microcirculations at the two monitored parts of body are different and the processing unit 505 is arranged to control the display 507 to show an alert message to inform the user to exercise the body.

In another embodiment, the processing unit 505 compares the first 3D energy distribution and the second 3D energy distribution with an energy threshold, and calculates a first area of the first 3D energy distribution having energy amplitudes larger than the energy threshold and a second area of the second 3D energy distribution having energy amplitudes larger than the energy threshold. The processing unit 505 monitors a variation of a ratio of or a difference between the first area and a second area, and controls the display 507 to show an alert message when the ratio or the difference changes to exceed a variation threshold.

It should mentioned that the physiological detection system of this embodiment may include more than two physiological detection devices to monitor different parts of body, and the processing unit 45 controls the display 47 to show a hint when the calculated multiple 3D energy distributions are not balance or have a significant difference.

In another embodiment, the vascular information in the superficial microcirculation of the skin can be detected in a non-optical manner (such as Doppler detection) as long as the required resolution is met. For example, the photosensitive pixel is preferably in a size from 5×5 µm to 10×10 µm, and the photosensitive array is preferably in a size from 240×240 µm to 480×480 µm. The detection is not limited to the optical detection. Namely, the physiological detection system always includes a sensor array and a processing unit irrespective of whether a light source is included. The sensor array is used to detect a microcirculatory data array in the dermis of the skin in order to reflect the states of different skin areas. The sensor array includes a plurality of pixel areas, which is in the form of a plurality of photosensitive pixels in an optical detection. In another detection mechanism, the plurality of pixel areas is in the form of a plurality of sensing pixels. In this regard, the processing unit determines different microcirculation states according to the changes of the microcirculatory data array over time. The changes of the microcirculatory data array include a change of the microcirculatory data array over time, as well as a change of the average value of the microcirculatory data array over time.

Monitoring other features of the microcirculation is also helpful to discover the peripheral vascular disease at early stage. For example, an oscillation frequency with time of arc-like patterns between FIGS. 6A and 6B reflects a frequency of a precapillary sphincter opening and closing the precapillary per minute. The present disclosure further provides a microcirculation detection system and method that do not adopt. Doppler method to detect a biphasic blood flow response. An oscillation frequency of an arc-like pattern detected by the microcirculation detection system of the present disclosure is different from the heart rate, and the oscillation frequency is about 5 to 10 times per minute.

Figure 10A:
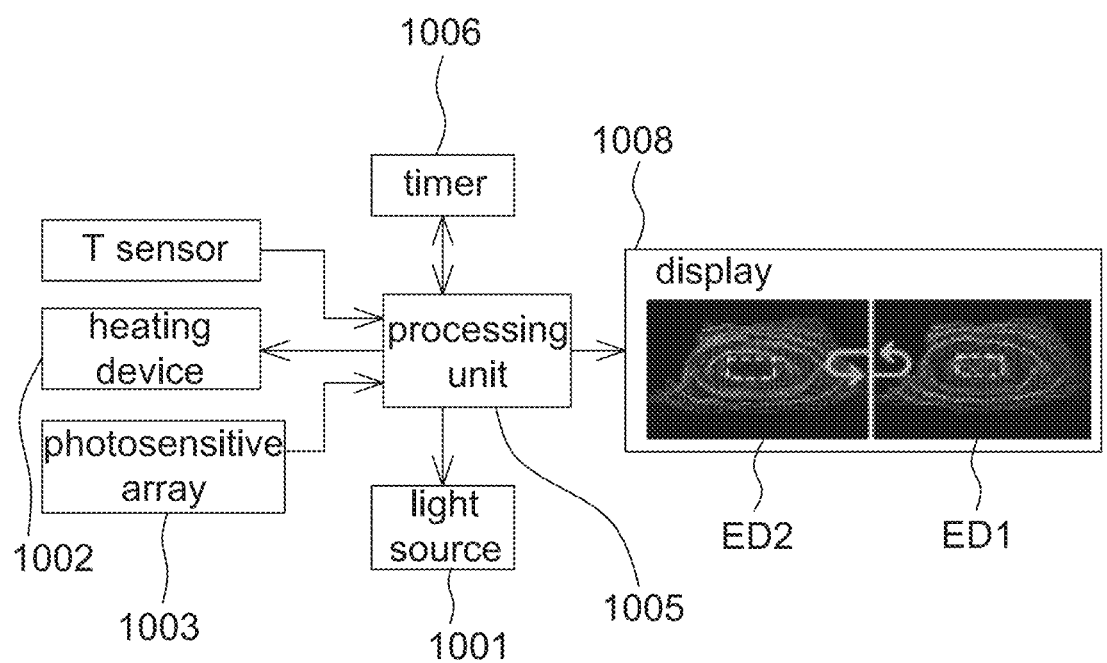
FIG. 10A is a block diagram of a microcirculation detection system according to one embodiment of the present disclosure.

Referring to FIG. 10A, it is a block diagram of a microcirculation detection system 1000 according to one embodiment of the present disclosure. Similar to the physiological detection system in FIG. 4, the microcirculation detection system 1000 of this embodiment also includes a light source 1001, a photosensitive array 1003 and a processing unit 1005, wherein the types of the light source 1001, the photosensitive array 1003 and the processing unit 1005 are respectively identical to the light source 41, the photosensitive array 43 and the processing unit 45 mentioned above and thus details thereof are not repeated herein.

The arrangement of the light source 1001 and the photosensitive array 1003 with respect to a skin surface is referred to FIG. 4 as an example. The light source 1001 is used to irradiate light to illuminate a skin area, wherein a wavelength of the light is preferably selected between 500 nm and 550 nm for detecting a tissue depth that the precapillary locates. The photosensitive array 1003 is used to detected outgoing light from the skin area and output a plurality of PPG signals, wherein each PPG signal is referred to FIG. 2B as an example. The photosensitive array 1003 includes a plurality of pixel areas arranged in a matrix (as shown in FIG. 2A for example), and the plurality of pixel areas is respectively used to output a brightness variation signal as one of the plurality of PPG signals, wherein each of the plurality of pixel areas includes at least one sensing pixel. When one pixel area includes multiple sensing pixels, the photosensitive array 1003 has a circuit used to sum up detected signals of the multiple sensing pixels of one pixel area to output a sum of brightness variation signals as a PPG signal of said one pixel area.

The processing unit 1005 also converts the plurality of PPG signals to an array energy distribution (e.g., the 3D energy distribution shown in FIG. 2D as an example), and identifies an arc-like pattern in the array energy distribution, e.g., identifying a first arc-like pattern ED1 (or the one shown in FIG. 6A) in the array energy distribution at a first time point, and a second arc-like pattern ED2 (or the one shown in FIG. 6B) in the array energy distribution at a second time point, wherein the first time point is different from the second time point. As mentioned above, the array energy distribution is an energy value distribution, corresponding to a two dimensional space of the plurality of pixel areas, of spectrum energies at a predetermined frequency (e.g., heart rate or a multiplication thereof) of the plurality of PPG signals. The arc-like pattern in the array energy distribution oscillates or fluctuates with time, e.g., between ED1 and ED2. When a skin surface temperature of a skin area under detection is substantially fixed, an oscillation frequency (times per minute) of the arc-like pattern is maintained at a substantially fixed value.

In addition, the microcirculation detection system 1000 of this embodiment further includes a heating device 1002 for heating the skin area, and a timer 1006 for counting a heating period of the heating device 1002. The timer 1006 is selected from known devices without particular limitations as long as the timer 1106 is controlled by the processing unit 1005 to start to count time when the heating device 1002 starts to heat the skin area. The processing unit 1005 further resets the timer 1006 before starting to count a heating period.

Figure 10B:
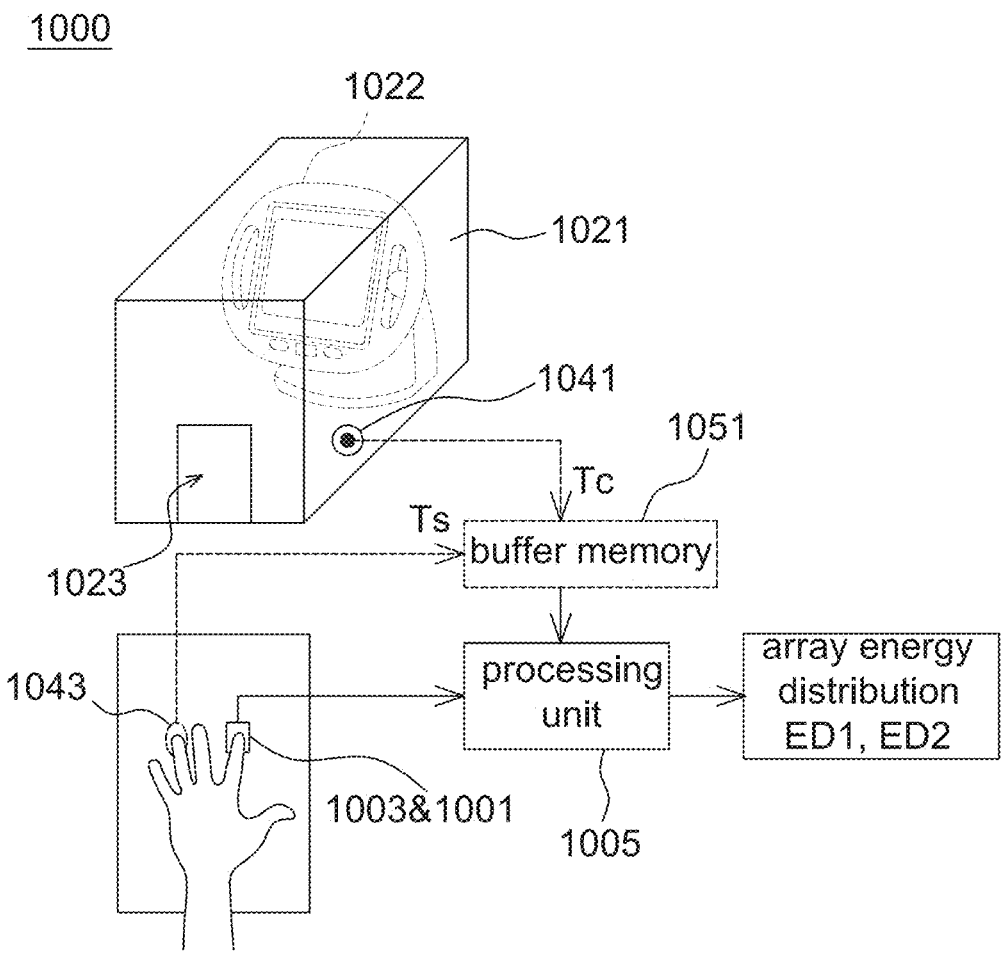
FIG. 10B is an operational schematic diagram of a microcirculation detection system according to one embodiment of the present disclosure.

Referring to FIG. 10B, it is an operational schematic diagram of a microcirculation detection system 1000 according to one embodiment of the present disclosure. In one non-limiting aspect, the heating device 1002 includes, for example, a heating chamber 1021 and a heater 1022. The heating chamber 1021 is used to accommodate the skin area. For example, when a skin area to be detected is at a hand of a user, the heating chamber 1021 has an opening 1023 for the user to put his/her hand into the heating chamber 1021 via the opening 1023. It is appreciated that when the heating chamber 1021 is used to accommodate other body part of the user (e.g., leg), the opening 1023 is arranged at different surfaces of the heating chamber 1021 such that the user can easily put in his/her body part therein for the detection.

The heater 1022 is, for example, an infrared heat lamp or an electric heating tube that is disposed inside the heating chamber 1021 for heating the gas inside the heating chamber 1021. The infrared heat lamp can also heat the skin area under detection with radiation heat. It is appreciated that when a user puts his/her hand into the heating chamber 1021, the skin area under detection is uniformly heated by the gas inside the heating chamber 1021. In other aspects, a contact type heater is used to directly increase a temperature at the skin area under detection. More specifically, the type of the heater 1022 is not particularly limited as long as it is able to increase the skin surface temperature.

Meanwhile, to record a skin surface temperature of the skin area under detection, the microcirculation detection system 1000 of this embodiment further includes a temperature sensor 1043 used to detect the skin surface temperature. One benefit of uniformly heating the user's hand is that a skin surface temperature on a different finger (e.g., FIG. 10B showing the fourth finger) measured by the temperature sensor 1043 is considered as the skin surface temperature of the skin area under detection (e.g., the second finger putting on the light source 1001 and the photosensitive array 1003 shown in FIG. 10B). The measured temperature Ts is sent to a buffer memory 1051 to be recorded and accessed by the processing unit 1005. In addition, the microcirculation detection system 1000 further includes a temperature sensor 1041 used to measure a chamber temperature Tc inside the heating chamber 1021, and the measured temperature Tc is sent to the buffer memory 1051 to be recorded and accessed by the processing unit 1005. The buffer memory 1051 is a volatile memory, and included in or outside of the processing unit 1005 without particular limitations.

Figure 11:
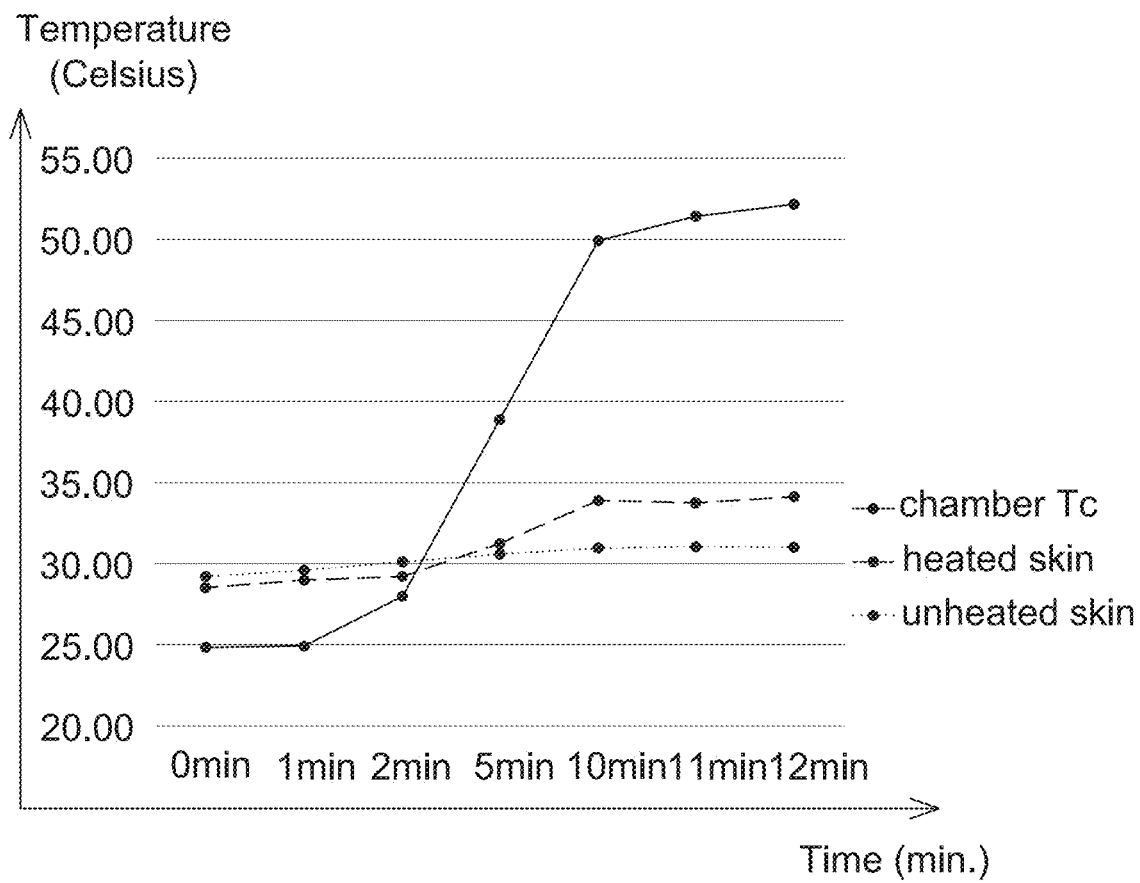
FIG. 11 is a schematic diagram of temperature heating of a microcirculation detection system according to one embodiment of the present disclosure.

Referring to FIG. 11, it is a schematic diagram of the chamber temperature Tc and the heated skin temperature (e.g., left hand shown in FIG. 10B) within a heating period of the microcirculation detection system 1000. In some aspects, it is an option to also record an unheated skin temperature (e.g., right hand) using another temperature sensor to confirm whether the skin heating process is normal or not. Generally, the heating period is set from 12 to 15 minutes depending on different users. It is seen from FIG. 11 that when the chamber temperature Tc increases, the heated skin is heated to a higher skin surface temperature.

In the process of heating the skin area under detection by the heating device 1002, the photosensitive array 1003 is used to continuously sense outgoing light from the skin area to output a plurality of PPG signals at different time points, and the plurality of PPG signals at each time point is used to form one array energy distribution. The processing unit 1005 identifies an arc-like pattern in each array energy distribution at a predetermined frequency (e.g., frame rate), and calculates a frequency variation of an oscillation of the arc-like pattern within the heating period.

In one non-limiting aspect, the oscillation of the arc-like pattern is identified by an energy amplitude oscillation at a position within the arc-like pattern of the energy array distribution corresponding to at least one of the plurality of pixel areas.

In another non-limiting aspect, the oscillation of the arc-like pattern is identified by a pattern oscillation between the first arc-like pattern ED1 and the second arc-like pattern ED2. For example, the processing unit 1005 firstly determines a first arc-like pattern ED1 and a second arc-like pattern ED2 to be stored in a frame buffer, wherein the first arc-like pattern ED1 and the second arc-like pattern ED2 are substantially out of phase from each other. During the heating period, the processing unit 1005 compares the similarity or correlation of every identified arc-like pattern with the stored first arc-like pattern ED1 and the second arc-like pattern ED2 to confirm the oscillation therebetween. When some arc-like patterns are alternatively identified as the first arc-like pattern ED1 and the second arc-like pattern ED2 (e.g., similarity or correlation higher than a threshold) within the heating period, it is able to calculate the oscillation frequency.

Figure 12:
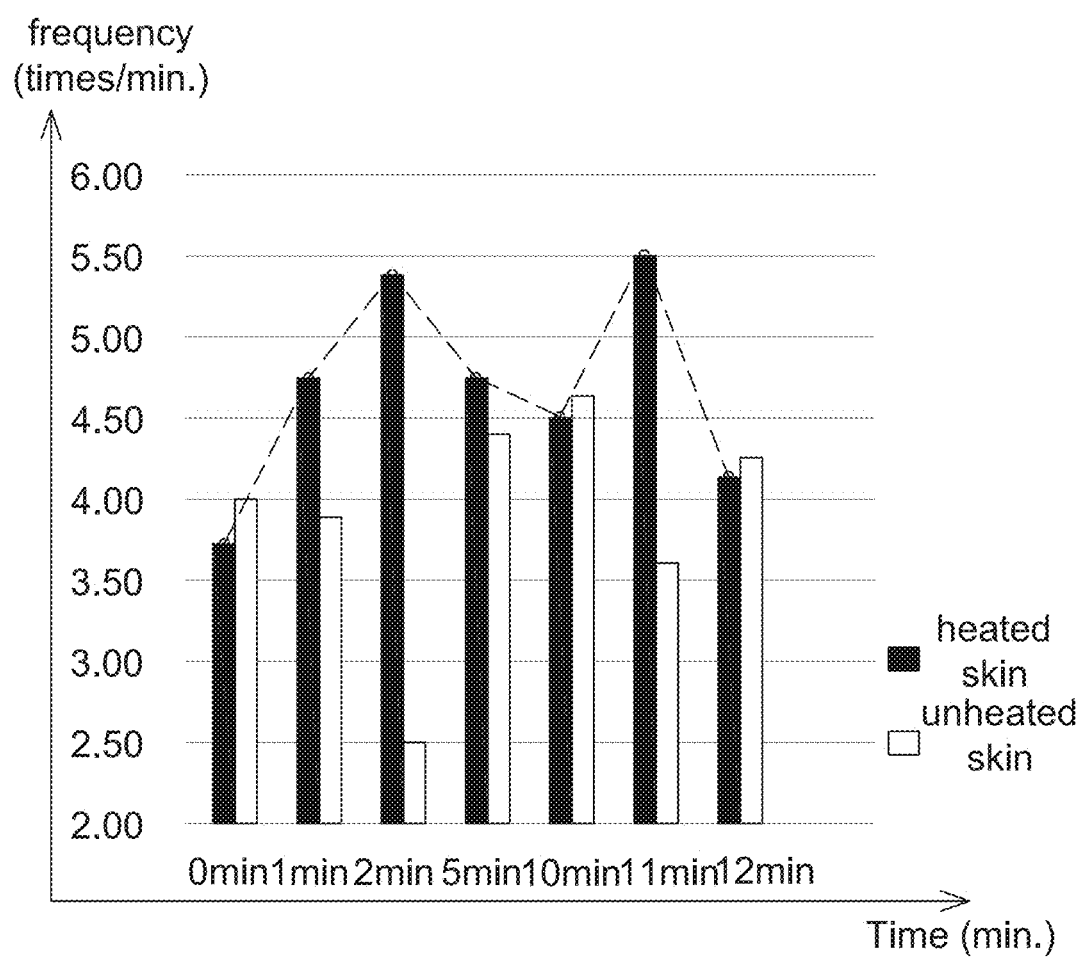
FIG. 12 is a schematic diagram of frequency variations detected by a microcirculation detection system according to one embodiment of the present disclosure.

For example referring to FIG. 12, it is a schematic diagram of the frequency variation detected by a microcirculation detection system 1000 according to one embodiment of the present disclosure. FIG. 12 shows that an oscillation frequency of the arc-like pattern has a peak (i.e. highest oscillation frequency) respectively at the second and the eleventh minutes after the heating is started, and this phenomenon is referred to the biphasic blood flow response. To detect these two phases (i.e., the two peaks), the processing unit 1005 further identifies whether a peak of the frequency variation (e.g., a change of oscillation times between ED1 and ED2 per minute) occurs respectively in a first time interval and a second time interval within a heating period, wherein the first time interval is selected as 2 to 5 minutes of the heating period, and the second time interval is selected as 10 to 15 minutes of the heating period. FIG. 12 further shows a frequency variation of the unheated skin as a comparison. In actual operation, the microcirculation detection system 1000 is arranged to only record a frequency variation of the arc-like pattern of the heated skin without recording the unheated skin.

In addition, the microcirculation detection system 1000 of this embodiment further includes an indication device 1008 for indicating the detected result using images, sounds, vibrations, lamps, wireless signals or the like. For example, when the indication device 1008 is a display, the display is used to show at least one of arc-like patterns at different time points (e.g., the first arc-like pattern ED1 and second arc-like pattern ED2 in FIG. 10A), the frequency variation (e.g., using histogram or line chart shown in FIG. 12), the heating period (e.g., by numbers or line chart), the chamber temperature and skin surface temperature (e.g., by numbers or line chart). When identifying that there is no peak value within at least one of the first time interval and the second time interval, it means that the blood flow control on microcirculation of the user may not be normal and thus the processing unit 1005 controls the indication device 1008 to generate an indication signal.

Figure 13:
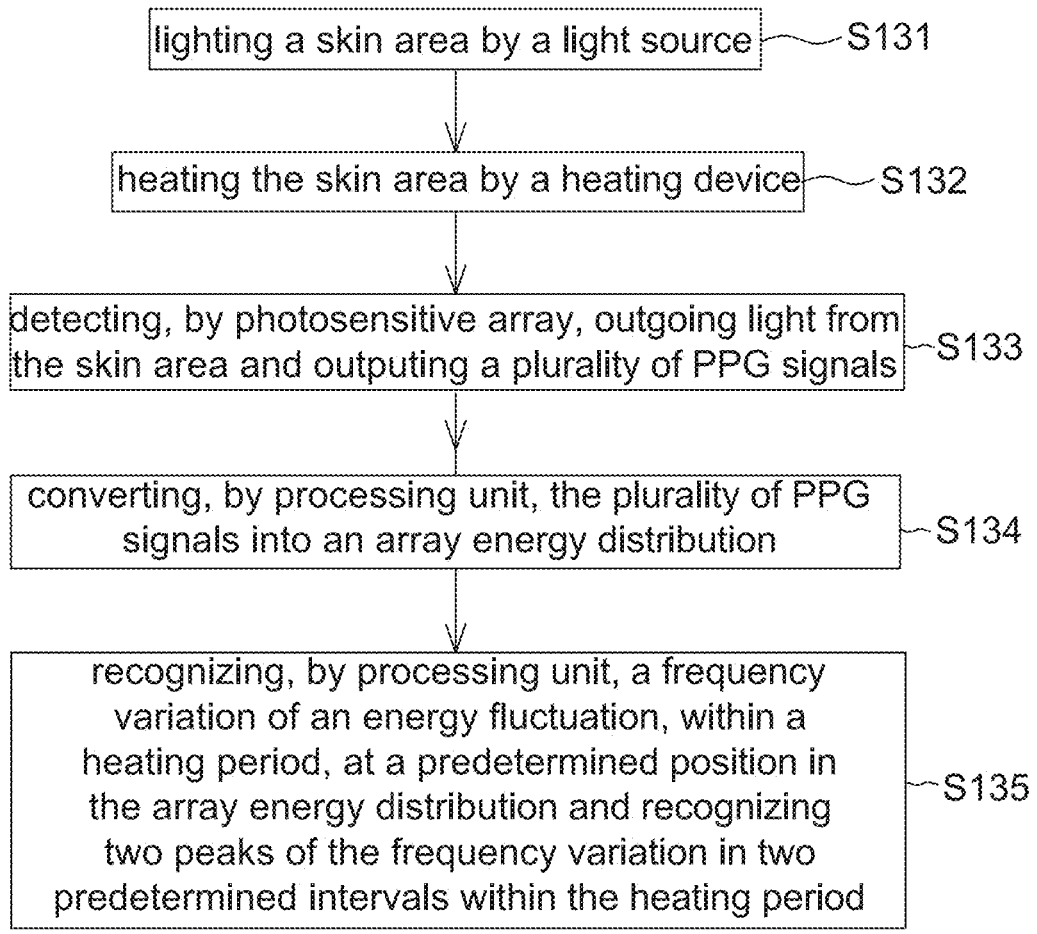
FIG. 13 is a flow chart of a detection method of a microcirculation detection system according to one embodiment of the present disclosure.

Referring to FIG. 13, it is a flow chart of a detection method of a microcirculation detection system according to one embodiment of the present disclosure. The detection method is adaptable to the microcirculation detection system 1000 of FIGS. 10A and 10B for instance. The detection method of this embodiment includes the steps of: lighting a skin area by a light source (Step S131); heating the skin area by a heating device (Step S132); detecting, by a photosensitive array, outgoing light from the skin area and outputting a plurality of PPG signals (Step S133); converting, by a processing unit, the plurality of PPG signals to an array energy distribution (Step S134); and recognizing, by the processing unit, a frequency variation of an energy fluctuation, within a heating period, at a predetermined position in the array energy distribution, and recognizing two peaks of the frequency variation in two predetermined intervals within the heating period (Step S135).

Firstly, the light source 1001 is turned on to illuminate a skin area, and the heating device 1002 starts to heat the skin area (Steps S131-S132). In one non-limiting aspect, the light source 2001 is arranged to emit light when the heating device 1002 is powered on. The light source 1001, the temperature sensor 1043 and the photosensitive array 1003 are directly arranged inside the heating chamber 1021, or they are firstly arranged on the user's body and then disposed in the heating chamber 1021.

In one non-limiting aspect, the photosensitive array 1003 is arranged to output a plurality of PPG signals when the heating device 1002 starts to heat the heating chamber 1021, wherein a number of the PPG signals is determined by a number of the pixel areas (Step S133).

The processing unit 1005 distributes spectrum energies at a predetermined frequency of the plurality of PPG signals on a two dimensional space corresponding to the plurality of pixel areas to form an array energy distribution, e.g., FIG. 10A showing array energy distributions at different time points as ED1 and ED2 (Step S134).

The processing unit 1005 is arranged to determine a predetermined position, e.g., a position within the array energy distribution corresponding to at least one of the plurality of pixel areas and having an energy oscillation exceeding an energy threshold such as a mass center, a gravity center or a center point of the arc-like pattern. The processing unit 1005 calculates a frequency variation of an oscillation frequency at the predetermined position within a heating period, as shown in FIG. 12 for example. As mentioned above, the processing unit 1005 identifies two peaks in two predetermined intervals (e.g., between 2 and 5 minutes and between 10 and 15 minutes) within the heating period (Step S135). When at least one of the predetermined intervals does not have the frequency variation peak, the processing unit 1005 controls the indication device 1008 to perform an indication. Besides, the display 1008 is used to show the calculated result of the processing unit 1005 including images of arc-like pattern, numbers or graphs of frequency variation, recorded temperatures and heating time. The processing unit 1005 further sends the calculated result to an external device via a communication interface or an Internet.

In the detection method herein, the processing unit 1005 calculates the frequency variation according to the oscillation or fluctuation between two selected art-like patterns as mentioned above.

In this embodiment, preferably the frequency variation is recorded after an arc-like pattern is identified at first. If the processing unit 1005 is not able to identify the arc-like pattern, the method such as changing the position of lighted light sources and adjusting the wearing tightness mentioned above can be performed at first in order to obtain an array energy distribution containing an arc-like pattern, and then the skin area is heated and detected. In the present disclosure, the arc-like pattern is similar to a water ripple generated by a stone falling into water.

The present disclosure is suitable for use in a transdermal drug delivery system. The transdermal drug delivery system refers to a drug administration where, after a transdermal drug delivery is made, the drug takes effect when guided through the skin in a certain speed, absorbed by the blood vessels during the microcirculation, and finally circulated in the human body. As a result, the first pass effect of the liver can be avoided, and the deterioration on the effect of the drug caused by the gastrointestinal tract is also prevented. Advantageously, the number of times of drug delivery is reduced, the interval between the drug deliveries is prolonged, and the effective serum concentration is maintained.

The present disclosure can be used to monitor the absorption condition of the drug in the microcirculatory blood vessels. Specifically, when the magnitude variation of the microcirculatory data increases and the heartbeat frequency becomes larger, it can be determined that the transdermal drug delivery system is functioning. To the contrary, when all of the magnitude variation, the heartbeat frequency, and the average magnitude value of the microcirculatory data have been restored to the normal ranges as they were, it can be determined that the functioning of the transdermal drug delivery system is completed. Thus, further treatment can be carried out, such as the second run of drug delivery. In other words, the array physiological detection system of the embodiment of the present disclosure is able to reflect the condition of drug delivery via the 3D spectral energy, thereby obtaining the effectiveness of the drug delivery.

Diabetic patients tend to have diseases such as atherosclerosis of native arteries of the extremities and peripheral neuropathy. The atherosclerosis of native arteries will cause the ischemic necrosis of the tissues, and the peripheral neuropathy will cause motor weakness and astereognosis. Since the microcirculatory blood vessels are innervated by sympathetic nerves, it is able to provide an early warning mechanism indicating whether the diabetic patients have contracted the aforementioned diseases via the supervision of the vascular change.

The present disclosure is able to monitor the vascular change of the microcirculatory blood vessels. When the microcirculation date presents a magnitude variation and an average value that decrease over time, it can be known that the functioning of the blood vessels is retrograding. In other words, the array physiological detection system of the embodiment of the present disclosure is able to reflect the degree of retrogression of the microcirculation, thereby obtaining the severity of illness.

The present disclosure is able to detect the pathological change of the patient. Specifically, an external excitation may be applied to the patient, and the microcirculatory response of the patient can be observed. For example, when observing whether the patient has a peripheral neuropathy, a cool and warm excitation is applied to the patient. In this regard, if the microcirculation presents a reduced magnitude variation and the heartbeat frequency does not increase, it indicates that the activity of the peripheral nerve is not high. In this case, a pathological change may be resulted.

The burned patients tend to have low blood capacity shock as well as increased fragility and permeability of the microcirculatory blood vessels due to the lack of local skin protection. In this situation, since the condition of the patients becomes worse quickly, the patients may have multiple organ dysfunction syndrome if the patients are not rescued in time. In this regard, the array physiological detection system of the embodiment of the present disclosure is able to detect the circulations of the peripheral tissues of the patients, thus monitoring the conditions of the patients and preventing the patients from a worse condition. In other words, the array physiological detection system of the embodiment of the present disclosure is able to reflect the operational status of the microcirculation via the 3D energy spectrum, thereby reflecting the change on the conditions of the patients.

It has been proven that the hyperbaric oxygen therapy is clinically effective in improving the microcirculations of the tissues after radiotherapy. The hyperbaric oxygen therapy exhibits an outstanding curative effect in treatment of radiative osteonecrosis and soft tissue necrosis. When the patient is receiving the hyperbaric oxygen therapy, the curative effect may be observed via the array physiological detection system of the present disclosure. Specifically, when the magnitude variation of the microcirculatory data increases and the heartbeat frequency becomes larger, it indicates that the activity of the microcirculatory blood vessels has been gradually recovered. The therapy is effective. In other words, the array physiological detection system of the embodiment of the present disclosure is able to reflect the recovering process of the microcirculation via the 3D energy spectra Therefore, the curative effect can be observed.

Shock is an ongoing phenomenon. When the tissues or organs of the human body are not provided with a sufficient amount of blood due to the inability of the circulation system to provide a proper metabolism, the tissues or organs in the body will have insufficient oxygen. As a result, the cell metabolism will be abnormal, causing a damage to, or death of, the cells. When the patient has a shock, the microcirculatory blood vessels will start to dilate. In this case, the condition of the patient may become worse if the situation is not properly handled.

When an alleviation mechanism is made to the shock, it can be observed whether the alleviation has taken effect or not through the use of the array physiological detection system of the embodiment of the present disclosure. If the average value of the magnitude signal is very large, the magnitude variation of the magnitude signal is not large and the heartbeat frequency remains relatively large, it indicates that the alleviation has not taken effect yet, and vice versa. In other words, the array physiological detection system of the embodiment of the present disclosure is able to reflect the recovering process of the microcirculation via the 3D energy spectrum. Therefore, the alleviation effect can be observed.

Heat exhaustion and heatstroke are typically seen in a case of excessively intensive exercise. In this situation, the blood circulation of the skin will increase. As a result, the amount of the blood that is pumped out by the heart should be increased. When the amount of blood is insufficient, the blood in the body will be reallocated such that the internal organs will be allocated with a smaller amount of blood and the skin tissues will be allocated with a larger amount of blood to facilitate the sweating process. As such, the heat in the body can be smoothly expelled. When the array physiological detection system of the embodiment of the present disclosure is used during the exercise, if it is detected that the average value of the magnitude signal is very large, the magnitude variation of the magnitude signal is not large, and the heartbeat frequency remains relatively large, the user will be reminded that he/she might have been in an intensive exercise and should take a break. In other words, the array physiological detection system of the embodiment of the present disclosure is able to reflect the blood allocation condition of the microcirculation via the 3D energy spectrum. Therefore, the cooling effect can be observed.

Microcirculation has the functions such as regulating the amount of the blood of the tissues, providing the cells with the nutrition, discharging the metabolite . . . etc. Through the array physiological detection system of the embodiment of the present disclosure, the corresponding temperature change of the peripheral tissue in the microcirculation can be detected. Namely, for the microcirculatory blood vessels of a local tissue, when the average value of the magnitude signal thereof is large, it indicates the temperature is increased, and vice versa. In other words, the array physiological detection system of the embodiment of the present disclosure is able to reflect the temperature condition of the microcirculation via the 3D energy spectrum. Therefore, the amount of blood in a local tissue can be observed.

For detecting the sympathetic nerves of the peripheral tissues of autistic patients, infants and pets, there has not been any useful and portable device available for detecting the microcirculatory blood vessels in the peripheral tissues. The blood vessel walls of the artery and arteriole of the microcirculatory blood vessels are formed by the smooth muscle. The artery and arteriole of the microcirculatory blood vessels are innervated by sympathetic nerves to control the opening and closing of the microcirculatory blood vessels, thereby determining the amount of blood supply of the tissues. Through the use of the array physiological detection system of the embodiment of the present disclosure, the activity of the sympathetic nerves may be surmised in an indirect manner. When the activity of the sympathetic nerves is high, the change of the microcirculatory blood vessels is also more obvious, and vice versa. In other words, the array physiological detection system of the embodiment of the present disclosure is able to reflect the condition of blood supply via the 3D energy spectrum. Therefore, the activity of the sympathetic nerves can be observed.

The array physiological detection system of the embodiment of the present disclosure can also be used to determine the functioning of the heart as well as detecting the systemic vascular defect and sclerosis. After all of the vascular dilation and constriction indication signals in the superficial microcirculation are integrated as a signal result, the signal result will have different energies under different frequencies. In general, the signals indicative of the energy is supposed to appear at the heartbeat frequency or a multiple of the heartbeat frequency while the energies of the signals will remain in a normal range. The range can vary from person to person. However, for the same user, the range should not have a significant change as time goes on. Therefore, if the signals indicative of the energy is at a frequency which is not a multiple of the heartbeat frequency or if the energies of the signals go out of the normal range as time passes, it indicates that the functioning of the heart or blood vessels of the user is abnormal. Further examination is required.

For example, when the signals indicative of the energy appears at a frequency which is not a multiple of the heartbeat frequency, it can indicate that the user has a cardiac dysfunction such as valve defect. When the energies of the signals have gone way beyond the normal range, it can indicate that the user has a vascular sclerosis. As a result, the heart needs to increase its power in pumping the blood throughout the body. In other words, the array physiological detection system of the embodiment of the present disclosure is able to reflect the abnormality of the microcirculation via the 3D energy spectrum. Therefore, the functioning of the heart can be observed.

In the above description, the magnitude variation refers to an energy variation of the 3D spectral energy, and the average value of the magnitude refers to an average value of the 3D spectral energy. The distribution of the 3D spectral energy is similar to what is shown in FIG. 2D. In addition, the quantity of the active pixels as mentioned above refers to a quantity of the pixels in the WOI. All of the values discussed in the specification are merely for explanation of the present disclosure and should not be used to limit the disclosure.

Although the present disclosure has been described in detail with reference to its presently preferable embodiment, it will be understood by one of ordinary skill in the art that various modifications can be made without departing from the spirit and the scope of the present disclosure, as set forth in the appended claims.

What is claimed is:

1. A microcirculation detection system, comprising:
   a light source configured to irradiate light to illuminate a skin area of a user;
   a heating device configured to heat the skin area within a heating period;
   a photosensitive array configured to detect outgoing light from the skin area and output a plurality of PPG signals; and
   a processing unit configured to
      convert the plurality of PPG signals to an array energy distribution,
      identify an arc-like pattern in the array energy distribution,
      calculate a frequency variation of an oscillation of the arc-like pattern within the heating period, and
      identify a peak value of the frequency variation respectively in two time intervals within the heating period in reflecting microcirculation of the user.

2. The microcirculation detection system as claimed in claim 1, wherein a wavelength of the light is between 500 nm and 550 nm.

3. The microcirculation detection system as claimed in claim 1, further comprising a display configured to show at least one of the arc-like pattern at different time points, the frequency variation, a heating temperature and a skin surface temperature.

4. The microcirculation detection system as claimed in claim 1, further comprising a timer configured to count the heating period.

5. The microcirculation detection system as claimed in claim 1, wherein the heating period is 15 minutes.

6. The microcirculation detection system as claimed in claim 1, wherein the heating device comprises:
   a heating chamber configured to accommodate the skin area; and
   an infrared heat lamp disposed inside the heating chamber and configured to heat the heating chamber.

7. The microcirculation detection system as claimed in claim 1, wherein the photosensitive array comprises a plurality of pixel areas arranged in a matrix and respectively configured to output a brightness variation signal as one of the plurality of PPG signals, wherein each of the plurality of pixel areas includes at least one sensing pixel.

8. The microcirculation detection system as claimed in claim 7, wherein the array energy distribution is an energy value distribution, corresponding to a two dimensional space of the plurality of pixel areas, of spectrum energies at a predetermined frequency of the plurality of PPG signals.

9. The microcirculation detection system as claimed in claim 8, wherein the oscillation of the arc-like pattern is an energy amplitude oscillation at a position within the arc-like pattern of the energy array distribution corresponding to at least one of the plurality of pixel areas.

* * * * *